(12) United States Patent
Sugenoya et al.

(10) Patent No.: US 8,391,946 B2
(45) Date of Patent: Mar. 5, 2013

(54) DEVICE AND METHOD FOR ACCURATELY MEASURING CONCENTRATION OF BLOOD COMPONENT

(75) Inventors: Junichi Sugenoya, Nagoya (JP); Yuzo Nakase, Moriya (JP); Satoshi Nakajima, Kyoto (JP); Muneo Tokita, Nagaokakyo (JP)

(73) Assignee: Omron Healthcare Co., Ltd., Kyoto (JP)

( * ) Notice: Subject to any disclaimer, the term of this patent is extended or adjusted under 35 U.S.C. 154(b) by 407 days.

(21) Appl. No.: 12/775,646

(22) Filed: May 7, 2010

(65) Prior Publication Data

US 2010/0234711 A1 Sep. 16, 2010

Related U.S. Application Data

(63) Continuation of application No. PCT/JP2008/070035, filed on Nov. 4, 2008.

(30) Foreign Application Priority Data

Nov. 9, 2007 (JP) ................................ 2007-292408

(51) Int. Cl.
*A61B 5/145* (2006.01)
(52) U.S. Cl. ....................................................... 600/346
(58) Field of Classification Search .................. None
See application file for complete search history.

(56) References Cited

U.S. PATENT DOCUMENTS

| 5,036,861 | A | 8/1991 | Sembrowich et al. | |
|---|---|---|---|---|
| 2002/0091312 | A1* | 7/2002 | Berner et al. | 600/347 |
| 2005/0069925 | A1 | 3/2005 | Ford et al. | |
| 2006/0004271 | A1 | 1/2006 | Peyser et al. | |
| 2006/0127964 | A1 | 6/2006 | Ford et al. | |
| 2006/0129035 | A1* | 6/2006 | Asano et al. | 600/300 |
| 2007/0027383 | A1 | 2/2007 | Peyser et al. | |
| 2007/0179371 | A1 | 8/2007 | Peyser et al. | |

FOREIGN PATENT DOCUMENTS

| JP | 61-135646 A | 6/1986 |
|---|---|---|
| JP | 62-72321 A | 4/1987 |
| JP | 2004-290523 A | 10/2004 |
| WO | 2005/018443 A1 | 3/2005 |
| WO | 2006/007472 A2 | 1/2006 |

OTHER PUBLICATIONS

J Appl Physiol. Dec. 1982;53(6):1540-5. Sweat composition in exercise and in heat. Verde T, Shephard RJ, Corey P, Moore R.*
Official Communication issued in corresponding Japanese Patent Application No. 2007-292408, mailed on Feb. 7, 2012.
Official Communication issued in International Patent Application No. PCT/JP2008/070035, mailed on Dec. 16, 2008.
Tokita, "Device for Accurately Measuring Concentration of Component in Blood and Control Method of the Device," U.S. Appl. No. 12/775,642, filed May 7, 2010.
Sugenoya et al., "Device and Method for Accurately Measuring Concentration of Blood Component," U.S. Appl. No. 12/775,648, filed May 7, 2010.

* cited by examiner

*Primary Examiner* — Michael Kahelin
*Assistant Examiner* — Mitchell Alter
(74) *Attorney, Agent, or Firm* — Keating & Bennett, LLP

(57) ABSTRACT

In a measurement computation device arranged in a measurement device, an elapse of a predetermined time is detected after acceleration of perspiration, and a concentration of a first component in the perspiration obtained thereafter is converted to concentration of the first component in blood.

7 Claims, 29 Drawing Sheets

(A)  (B)

DEVICE AND METHOD FOR ACCURATELY MEASURING CONCENTRATION OF BLOOD COMPONENT

BACKGROUND OF THE INVENTION

1. Field of the Invention

The present invention relates to devices and methods for measuring the concentration of a blood component, in particular, to a device and a method for measuring the concentration of a blood component using perspiration.

2. Description of the Related Art

A method of measuring the concentration of a component in the blood such as blood glucose without collecting blood includes a method of measuring based on the concentration of a component contained in perspiration. For instance, U.S. Pat. No. 5,036,861 and Japanese Laid-Open Patent Publication No. 62-72321 describe such a method and device.

Specifically, as a method of forcibly perspiring, U.S. Pat. No. 5,036,861 discloses a medical agent introducing method, that is, a method of introducing the medical agent to a target area, and Japanese Laid-Open Patent Publication No. 62-72321 discloses a warming method, that is, a method of warming the target area. Japanese Laid-Open Patent Publication No. 62-72321 also describes that the perspiration sugar and the blood glucose are correlated.

However, a change in concentration of the sugar concentration in the perspiration is not necessarily correlated with the change in concentration of the blood glucose value. This is also apparent from the graph showing the correlation of the perspiration sugar and the blood glucose shown in Japanese Laid-Open Patent Publication No. 62-72321.

The inventors performed a measurement of the sugar concentration in the perspiration (referred to as perspiration sugar value) and the sugar concentration in the blood (blood glucose value) of after forced perspiration, and obtained a plurality of samples as shown in FIG. 19 to FIG. 26. FIG. 19 to FIG. 22 show samples of a change in concentration between the perspiration sugar value and the blood glucose value in a case where the perspiration is continuously collected after the perspiration acceleration of one time, and respectively shows samples of the measurement value obtained from different subjects. FIG. 24 to FIG. 26 show samples of a change in concentration of the perspiration sugar value obtained from the perspiration from after 0 minutes from the perspiration acceleration until elapse of five minutes, the perspiration sugar value obtained from the perspiration from after elapse of five minutes to elapse of ten minutes, and the blood glucose value by repeating perspiration acceleration with respect to the same subject, and respectively show samples of the measurement value obtained from different subjects.

The inventors verified the samples shown in FIG. 19 to FIG. 22, and found in particular that the change in concentration thereof is not correlated at the beginning of forced perspiration, and that the concentration of the perspiration sugar value rapidly lowers more greatly in the relevant period than in the period after the beginning.

FIG. 23 is a view showing a sample obtained by performing a measurement of the perspiration sugar value and the blood glucose value after exercise perspiration. Measurement after accumulating the perspiration for ten minutes is repeated three times to obtain such a sample. As shown in FIG. 23, in the exercise perspiration as well, the perspiration sugar value at the beginning of perspiration is at high concentration and the concentration changes differently from the change in blood glucose value, similar to the forced perspiration shown in FIG. 19 to FIG. 22. In other words, it is apparent from FIG. 19 to FIG. 23 that the component concentration in the perspiration at the beginning of perspiration is high concentration compared to the subsequent concentration regardless of the perspiration method.

Furthermore, it is verified from the samples shown in FIG. 24 to FIG. 26 that the opening from the change in concentration of the blood glucose value is greater and the correlation is not as found in the change in concentration of the perspiration sugar value obtained from the perspiration from after 0 minutes immediately after the perspiration acceleration until elapse of five minutes than the change in concentration of the perspiration sugar value obtained from the perspiration from after elapse of five minutes until elapse of ten minutes after the perspiration acceleration.

Therefore, when estimating the sugar concentration in the blood using the sugar concentration in the perspiration, the accuracy of the sugar concentration in the blood lowers particularly if the sugar concentration in the perspiration at the beginning of perspiration is used. Similar problems are found when the blood component is other components other than sugar.

SUMMARY OF THE INVENTION

In view of such problems, preferred embodiments of the present invention provide a device and a method capable of accurately measuring the concentration of a blood component using perspiration.

In accordance with a preferred embodiment of the present invention, a blood component concentration measurement device includes: a perspiration accelerating unit arranged to accelerate perspiration from a body surface or a measurement site; a first measurement unit arranged to measure a concentration in the perspiration of a first component contained in the perspiration from the measurement site; a detecting portion arranged to detect an elapse of a predetermined time after acceleration of the perspiration; and a converting portion arranged to convert the concentration in the perspiration of the first component contained in the perspiration from the measurement site after the elapse of the predetermined time to concentration of the first component in blood of the body, wherein the detecting portion includes, a calculating portion arranged to calculate a rate of change of the concentration of a component in the perspiration, and a determining portion arranged to compare the rate of change and a threshold value and to determine the elapse of the predetermined time when the rate of change is smaller than the threshold value.

In accordance with another preferred embodiment of the present invention, a blood component measurement method performed by a blood component concentration measurement device which includes an acquiring device arranged to acquire perspiration from a measurement site, a detection device arranged to detect a component in the perspiration, and a computation device arranged to perform a computation using a value obtained from the component, the method including the steps of: calculating a rate of change of concentration of a component in the perspiration with the computation device; detecting a first component from the perspiration with the detection device after the rate of change and a threshold value are compared and the rate of change becomes smaller than the threshold value; calculating a concentration in the perspiration of the first component with the computation device; converting the calculated concentration in the perspiration of the first component to a concentration of the first component in blood of the body; and executing a process of outputting the concentration in the blood of the first component with the computation device.

According to various preferred embodiments of the present invention, the concentration of the blood component can be accurately measured using perspiration.

Other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
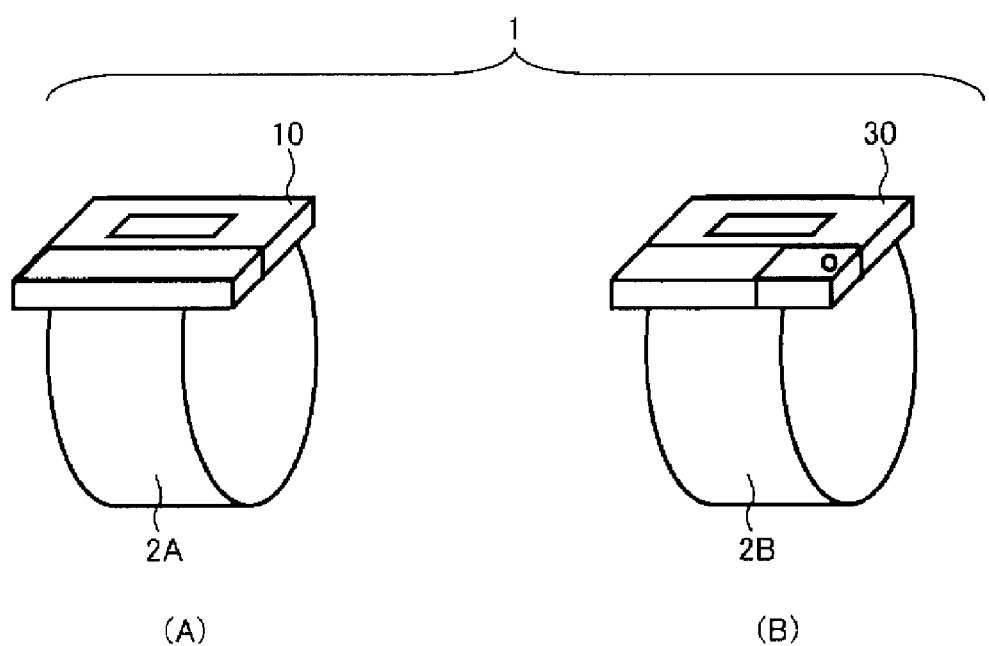
FIG. 1 is a view showing a specific example of an outer appearance of a measurement device according to the preferred embodiment, where (A) portion is a view showing a specific example of an outer appearance of a perspiration device and (B) portion is a measurement computation device 30.

Hereafter, the preferred embodiments of the present invention will be described with reference to the drawings. In the following description, the same reference numerals are denoted for the same components and the configuring elements. The names and functions thereof are the same.

First Preferred Embodiment

FIG. 1 is a view showing a specific example of an outer appearance of a blood component concentration measurement device (hereinafter abbreviated as measurement device) 1 according to the present preferred embodiment. The measurement device 1 includes a perspiration device 10 ((A) portion of FIG. 1) and a measurement computation device 30 ((B) portion of FIG. 1). The perspiration device 10 and the measurement computation device 30 are used by being attached to measurement sites such as a wrist and an ankle with belts 2A and, 2B, respectively.

Figure 2A:
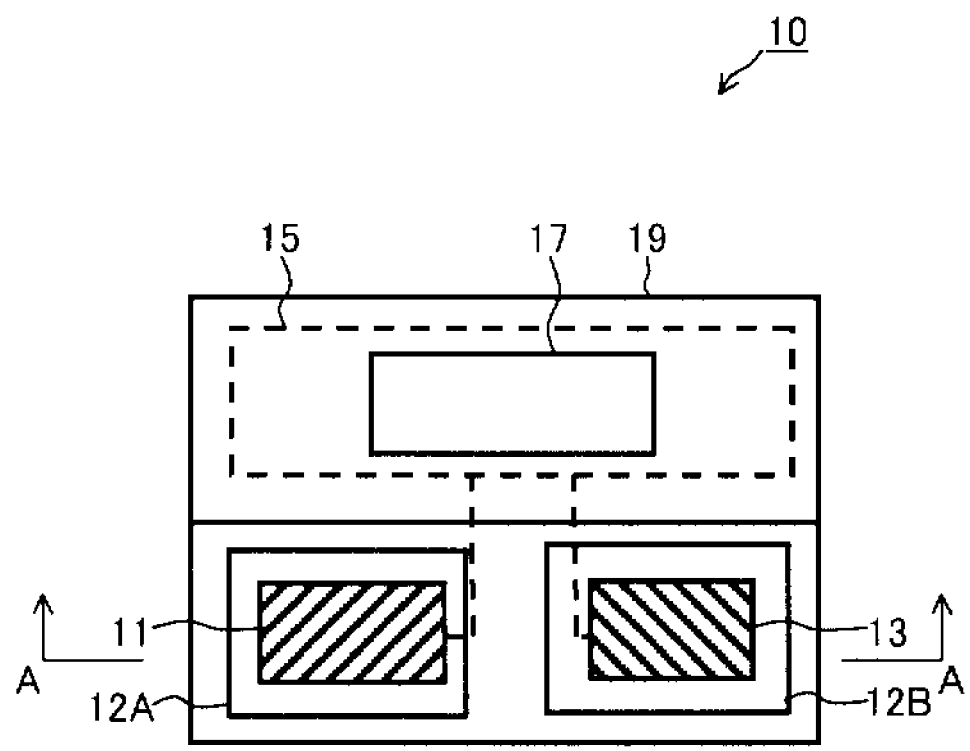
FIG. 2A is a view showing a specific example of a mechanical configuration of the perspiration device according to a preferred embodiment of the present invention seen from the front surface.

Specifically, with reference to FIG. 2A, the perspiration device 10 includes an introducing electrode 11 serving as an anode, and a reference electrode 13 serving as a cathode, inside a housing 19. The introducing electrode 11 and the reference electrode 13 are connected to a control circuit 15. A display 17 is arranged at a position that can be visually recognized in a state of being attached to the measurement site using the belt 2A on the housing 19 such as the surface shown on the upper side at the (A) portion of FIG. 1. The display 17 is also connected to the control circuit 15. FIG. 2A is a schematic view of the perspiration device 10 seen from the surface shown on the upper side at the (A) portion of FIG. 1. The surface shown in FIG. 2A is a front surface of the housing 19 of the perspiration device 10. An operation unit such as a button (not shown) is arranged at the front surface of the housing 19. The operation unit is also connected to the control circuit 15.

Figure 2B:
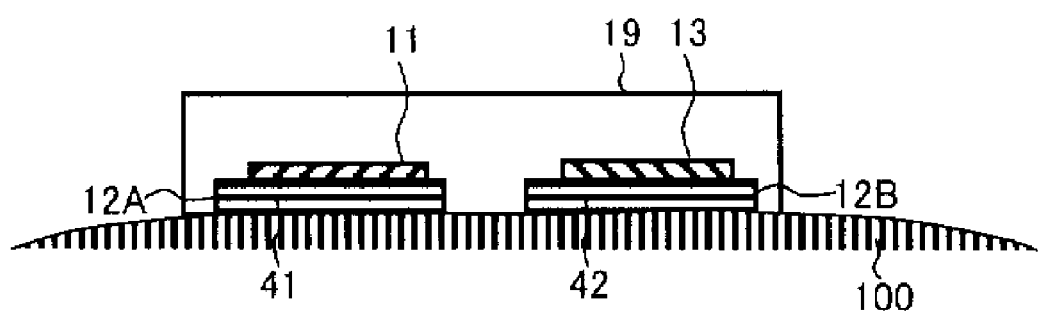
FIG. 2B is a view showing a cross-section at a position of an arrow A of FIG. 2A of a mechanical configuration of the perspiration device according to a preferred embodiment of the present invention.

FIG. 2B is a schematic view of a mechanical configuration of the cross-section of the perspiration device 10 at the position shown with an arrow A in FIG. 2A. With reference to FIG. 2B, the introducing electrode 11 and the reference electrode 13 are arranged at positions close to the surface on the far side from the front surface of the housing 19 in the housing 19, that is, at the positions close to the skin 100 serving as the measurement site in a state where the perspiration device 10 is attached to the measurement site using the belt 2A. Medical agent regions 12A, 12B are arranged between the introducing electrode 11 and the skin 100 and between the reference electrode 13 and the skin 100, respectively, of the housing 19. The medical agent region 12A is preferably set with a member or material such that the perspiration accelerator contacts the skin, such as a sponge 41 including liquid containing medical agent (perspiration accelerator) to accelerate perspiration, such as pilocarpine solution, for example. The medical agent region 12B is preferably set with a buffer such as a sponge 42 containing buffer solution. The medical agent regions 12A, 12B may have a configuration in which the medical agent is injected as is, a configuration in which the gelatinized medical agent is set, or a configuration in which the medical agent absorbed to absorbent cotton and the like is set. The configurations of the medical agent regions 12A, 12B may be any configuration as long as the medical agent set in the medical agent regions 12A, 12B contact the skin 100 in a state where the perspiration device 10 is attached to the measurement site.

The control circuit 15 stores current values in advance. When a control signal for starting the perspiration is input from the operation unit, the control circuit 15 generates a DC current with a specified current value from the introducing electrode 11 to the reference electrode 13 according to the control signal.

Figure 3A:
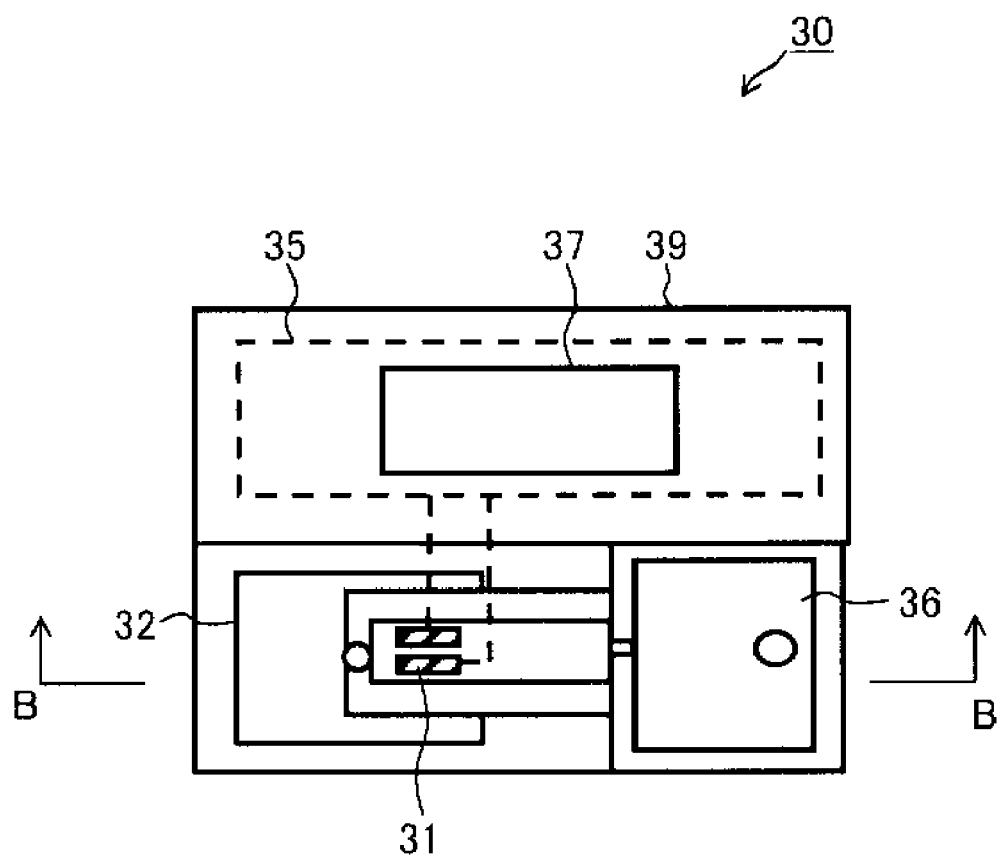
FIG. 3A is a view showing a specific example of a mechanical configuration of the measurement computation device according to a preferred embodiment of the present invention seen from the front surface.

With reference to FIG. 3A, the measurement computation device 30 according to the present preferred embodiment includes a first component detector 31 arranged to detect a first component in the perspiration in the housing 39, and is connected to the control circuit 35. A display 37 is arranged at a position that can be visually recognized in a state of being attached to the measurement site using the belt 2B on the housing 39 such as the surface shown on the upper side at the (B) portion of FIG. 1. The display 37 is also connected to the control circuit 35. FIG. 3A is a schematic view of the measurement computation device 30 seen from the surface shown on the upper side at the (B) portion of FIG. 1. The surface shown in FIG. 3A is a front surface of the housing 39 of the measurement computation device 30. An operation unit such as a button (not shown) is arranged at the front surface of the housing 39. The operation unit is also connected to the control circuit 35.

Figure 3B:
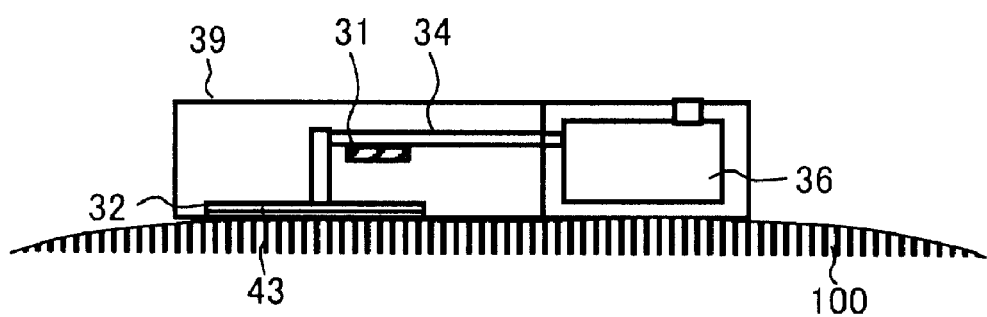
FIG. 3B is a view showing a cross-section at a position of an arrow B of FIG. 3A of a mechanical configuration of the measurement computation device according to a preferred embodiment of the present invention.

FIG. 3B is a schematic view of a mechanical configuration of the cross-section of the measurement computation device 30 at the position shown with an arrow B in FIG. 3A. With reference to FIG. 3B, a perspiration collection region 32 is arranged at a position close to the surface on the far side from the front surface of the housing 39 in the housing 39, that is, at a position close to the skin 100 serving as the measurement site in a state where the measurement computation device 30 is attached to the measurement site using the belt 2B. The perspiration collection region 32 is preferably set with a member or material to collect perspiration from the skin 100, such as a sponge 43 for collecting perspiration. The perspiration collection region 32 may have a configuration of collecting perspiration directly from the skin 100, or a configuration in which a medical agent for gelatinizing the perspiration is set. The configuration of the perspiration collection region 32 may be any configuration as long as the perspiration can be collected from the skin 100 in a state where the measurement computation device 30 is attached to the measurement site. Furthermore, a discarding liquid storage unit 36 arranged to store discarded liquid after component detection is arranged inside the housing 39 of the measurement computation device 30. A conveyance path 34 is arranged to convey the perspiration from the perspiration collection region 32 to the discarding liquid storage unit 36 through the first component detector 31.

Figure 4:
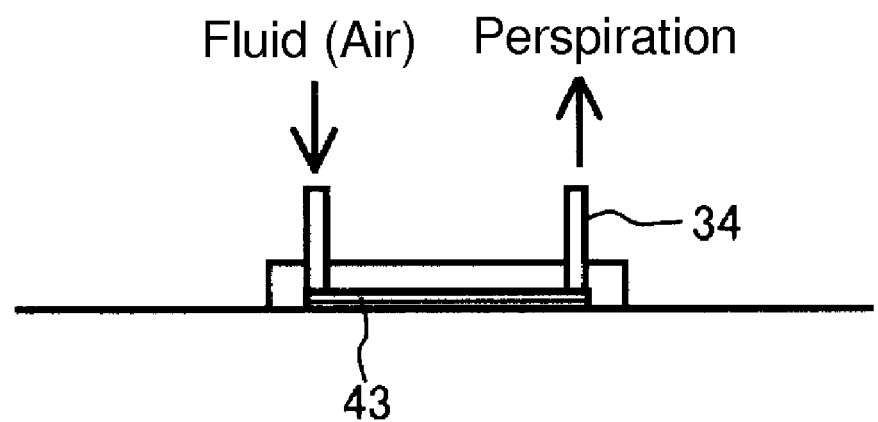
FIG. 4 is a view describing one example of a method of conveying the perspiration from the perspiration collection region to the discarding liquid storage unit in the measurement computation device.

The present invention is not limited to the conveyance path 34 to convey the perspiration as described above, and a method of injecting fluid such as air from one side of the conveyance path 34 including the perspiration collection region 32 and pushing out the internal perspiration to the other side, as shown in FIG. 4, may be adopted.

Figure 5:
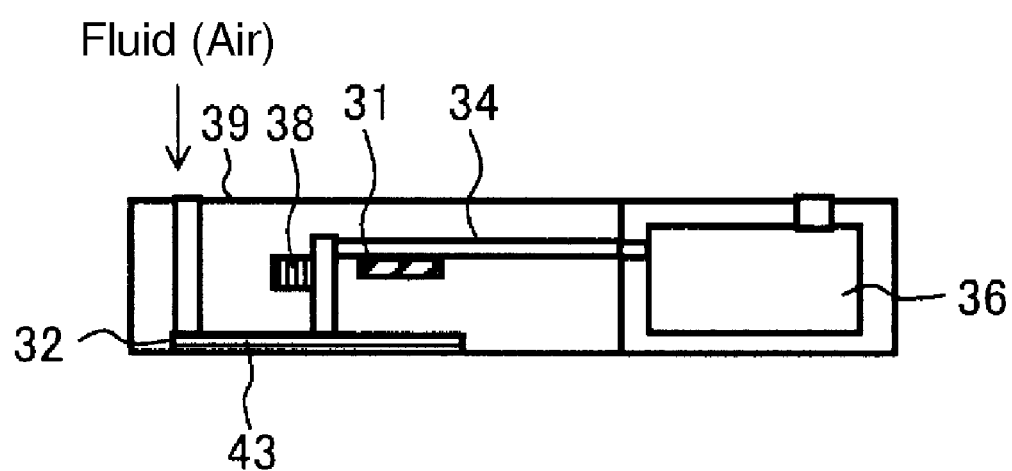
FIG. 5 is a view showing another specific example of a mechanical configuration of the measurement computation device.

The mechanical configuration shown in FIGS. 2A, 2B, 3A, 3B is a specific example, and the configurations of the perspiration device 10 and the measurement computation device 30 are not limited to the illustrated configurations. For instance, as another specific example of the configuration of the measurement computation device 30, a liquid sensor 38 arranged to detect the perspiration amount that is collected by the perspiration collection region 32 and that reached the conveyance path 34 may be arranged, as shown in FIG. 5, to convey the perspiration in the conveyance path 34. In this case, when detecting that the collected perspiration amount reached a predetermined amount based on the detection signal from the liquid sensor 28, the control circuit 35 outputs a control signal to a mechanism for injecting fluid such as compressed air (not shown) to the conveyance path 34, and conveys the perspiration of the perspiration collection region 32 to the first component detector 31. Furthermore, the perspiration at the first component detector 31 is conveyed to the discarding liquid storage unit 36 after component detection is performed in the first component detector 31.

As another specific example of the configuration of the measurement device 1, the perspiration device 10 and the measurement computation device 30, which are separate devices, shown in FIG. 1 may be used by being replaced with respect to one belt 2. In this case, the control circuit and the display may be commonly used by the perspiration device 10 and the measurement computation device 30. With such a configuration, the perspiration device 10 and the measurement computation device 30 are attached to the same measurement site, and thus the perspiration can be efficiently collected from the same position as the portion where perspiration is accelerated by the perspiration device 10. As another configuration, in the display 17, the elapsed time from when the perspiring operation is started may be displayed when the perspiring operation starts in the perspiration device 10.

The first component is a component that becomes a target of calculating the blood concentration, and corresponds to a component in which the change in concentration in the perspiration and the change in concentration in the blood are related. Specifically, this corresponds to sugar (glucose), where the first component is sugar in the present preferred embodiment.

The first component detector 31 of the measurement computation device 30 has a configuration to detect the component in the perspiration, but is not limited to a specific configuration. For instance, the component may be detected by measuring the wavelength of the radiation light, or an enzyme electrode method may be used. The configuration corresponding to the first component to be measured may be adopted. If the first component detector 31 uses the enzyme electrode method, the measurement computation device 30 can be miniaturized compared to other configurations such as the configuration of measuring the wavelength of the radiation light. The first component detector 31 in the present preferred embodiment may have a configuration combining glucose oxidase and electrode using the enzyme electrode method to detect sugar as the first component.

Figure 6:
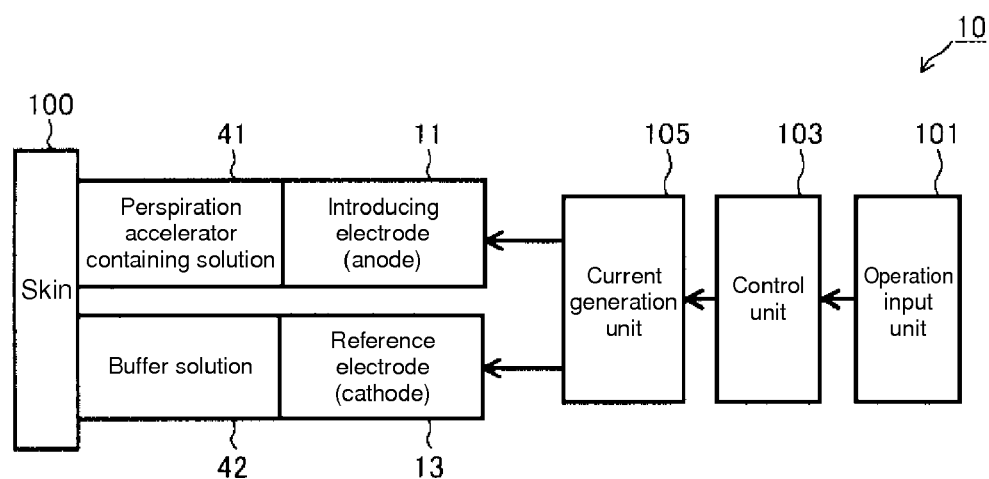
FIG. 6 is a block diagram showing a specific example of the function configuration of the perspiration device according to a preferred embodiment of the present invention.
Figure 7:
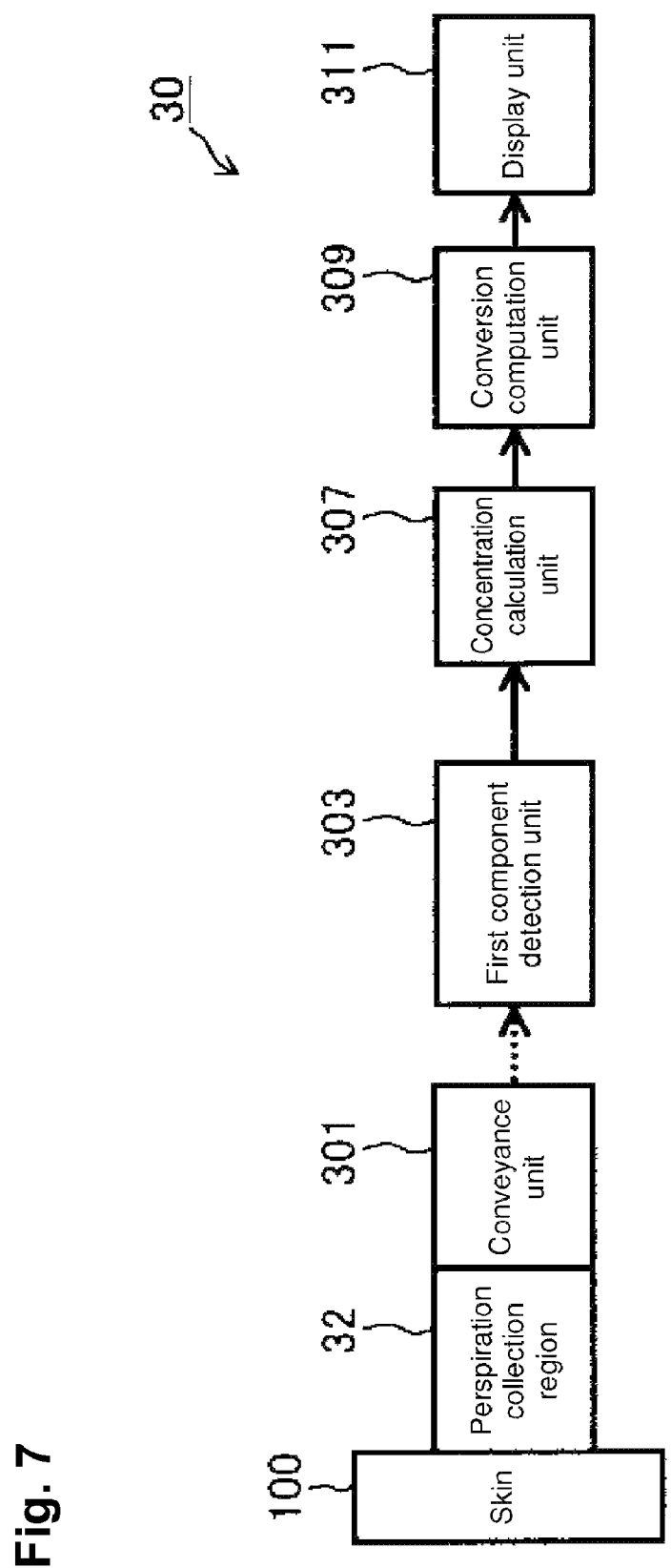
FIG. 7 is a block diagram showing a specific example of the function configuration of the measurement computation device according to a preferred embodiment of the present invention.

FIG. 6 and FIG. 7 are block diagrams showing a specific example of the function configuration for collecting the perspiration from the skin 100 and calculating the concentration of the first component in the blood using the concentrations of the first component and the second component in the perspiration in the measurement device 1 including the perspiration device 10 and the measurement computation device 30. FIG. 6 shows a specific example of the perspiration device 10. FIG. 7 shows a specific example of the function configuration of the measurement computation device 30. Each function shown in FIG. 6 and FIG. 7 is a function implemented when the control circuit 15 of the perspiration device 10 and the control circuit 35 of the measurement computation device 30 execute a predetermined control program. At least one portion of such functions maybe implemented by the mechanical configuration shown in FIGS. 2A, 2B or FIGS. 3A, 3B. The solid line arrow in FIG. 6 and FIG. 7 shows a flow of electric signal. The dotted line arrow in FIG. 7 shows the conveyance of perspiration.

With reference to FIG. 6, the function of the perspiration device 10 includes an operation input unit 101 arranged to accept the input of the operation signal from the operation unit (not shown in FIG. 1, and FIGS. 2A, 2B), a control unit 103, and a current generation unit 105.

The control unit 103 is mainly configured by the control circuit 15, and starts the perspiring operation based on the operation signal input from the operation input unit 101. The perspiring operation starts when the control unit 103 inputs the control signal to generate a current of a defined value based on the operation signal to the current generation unit 105. The current generation unit 105 is also mainly configured by the control circuit 15, and performs the process of generating the current of the defined value between the introducing electrode 11 and the reference electrode 13 according to the control signal. Through such process, the DC current flows from the introducing electrode 11 towards the reference electrode 13, passing through the skin 100 through the sponge 41 containing the pilocarpine solution or the solution containing the perspiration accelerator. Thus, the pilocarpine solution or the substance of the introducing electrode 11 is introduced by being infiltrated under the skin, and acts on the perspiratory gland. Such method of introducing the substance is referred to as iontophoresis method.

When a predetermined time elapses from the start of perspiring operation, the perspiration occurs from the perspiratory gland near the introducing electrode 11. When the pilocarpine solution is infiltrated after elapse of a constant time from the start of the perspiring operation in the perspiration device 10, the control signal 103 outputs a control signal for stopping the generation of current to the current generation unit 105 according to the operation signal to terminate the perspiring operation from the operation input unit 101, and terminates the perspiring operation. The perspiring operation may be terminated when the control unit 103 detects elapse of a constant time from the start of the perspiring operation and outputs the control signal to stop the generation of current to the current generation unit 105.

With reference to FIG. 7, the function of the measurement computation device 30 according to the first preferred embodiment includes a conveyance unit 301 arranged to convey the perspiration accommodated in the perspiration collection region 32, a first component detection unit 303 arranged to detect the first component in the perspiration, a concentration calculation unit 307 arranged to calculate the concentration of the first component in the perspiration based on the detection signal from the first component detection unit 303, a conversion computation unit 309 arranged to perform a computation for obtaining the concentration of the first component in the blood using the calculation result, and a display unit 311 arranged to perform a process of displaying the computation result.

The conveyance unit 301 is configured by the conveyance mechanism as described above, and conveys the perspiration accommodated in the perspiration collection region 32 to the discarding liquid storage unit 36 through the first component detector 31. In the case of the configuration in which the measurement computation device 30 injects fluid such as compressed air to the conveyance path 34 to convey the perspiration accommodated in the perspiration collection region 32, the conveyance unit 301 includes a mechanism arranged to inject fluid to the conveyance path 34. Specifically, when injecting fluid by operation a mechanical configuration such as a pump, the conveyance unit 301 includes the mechanical configuration and the configuration to output a control signal for operating the configuration.

The first component detection unit 303 mainly includes the first component detector 31. The first component detection unit 303 detects the first component using the first component detector 31 from the perspiration conveyed by the conveyance unit 301, and inputs the detection signal corresponding to the detection amount to the concentration calculation unit 307.

The concentration calculation unit 307 is mainly configured by the control circuit 35, and calculates the concentration of the first component in the perspiration based on the detection signal input from the first component detection unit 303 according to a predetermined computation program. The signal indicating the calculated concentration is input to the conversion computation unit 309.

The conversion computation unit 309 is mainly configured by the control circuit 35, and performs a computation to convert the concentration of the first component in the perspiration to the concentration of the first component in the blood according to a predetermined computation program. The computation result is input to the display unit 311, and a process of displaying the concentration of the first component in the blood on the display 37 as a computation result is performed at the display 37.

Figure 8:
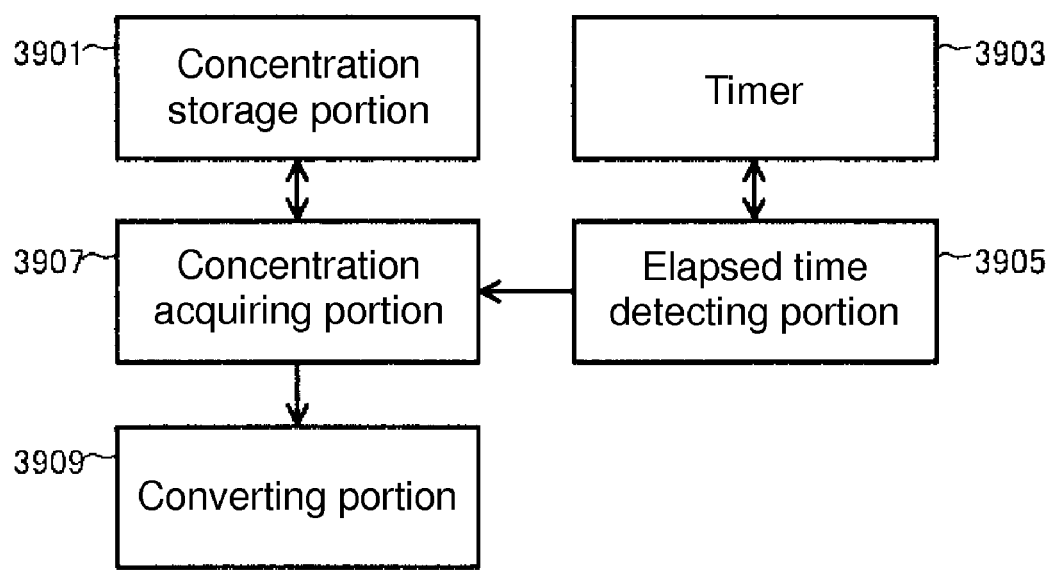
FIG. 8 is a block diagram showing a specific example of a detailed configuration of a conversion computation unit of the measurement computation device according to a preferred embodiment of the present invention.

FIG. 8 is a block diagram showing a specific example of a detailed configuration of the conversion computation unit 309 according to the first preferred embodiment. With reference to FIG. 8, the conversion computation unit 309 includes a concentration storage portion 3901 arranged to store the concentration input from the concentration calculation unit 307, a timer 3903, an elapsed time detecting portion 3905 arranged to detect that a predetermined time has elapsed using the timer 3903, a concentration acquiring portion 3907 arranged to acquire the concentration stored in the concentration storage portion 3901, and a converting portion 3909 arranged to convert the acquired concentration of the first component in the perspiration to the concentration of the first component in the blood.

The elapsed time detecting portion 3905 detects that the predetermined time defined in advance has elapsed using the timer 3903, and inputs a signal indicating the same to the concentration acquiring portion 3907. After such signal is input, the concentration acquiring portion 3907 acquires the concentration of the first component in the perspiration input from the concentration calculation unit 3901 and stored in the concentration storage portion 3901 from the concentration storage portion 3901, and inputs the same to the converting portion 3909.

Figure 24:
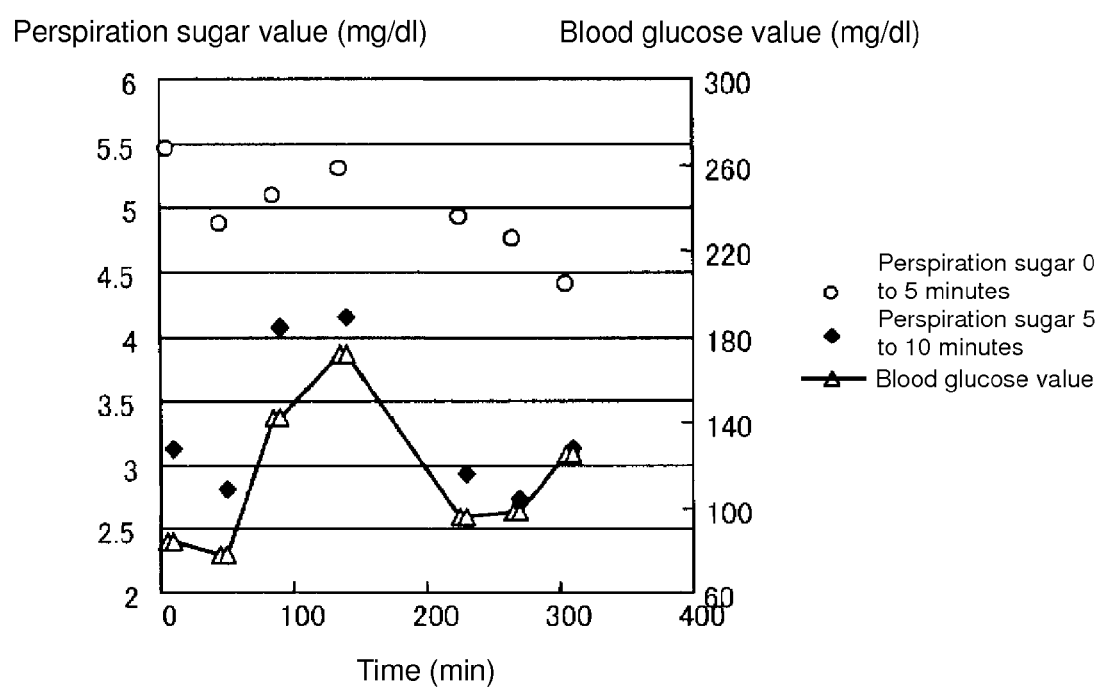
FIG. 24 is a view showing a sample of change in concentration of the perspiration sugar value obtained from the perspiration from after 0 minutes from the perspiration acceleration until elapse of five minutes, the perspiration sugar value obtained from the perspiration from after elapse of five minutes to elapse of ten minutes, and the blood glucose value by repeating perspiration acceleration with respect to the same subject.
Figure 25:
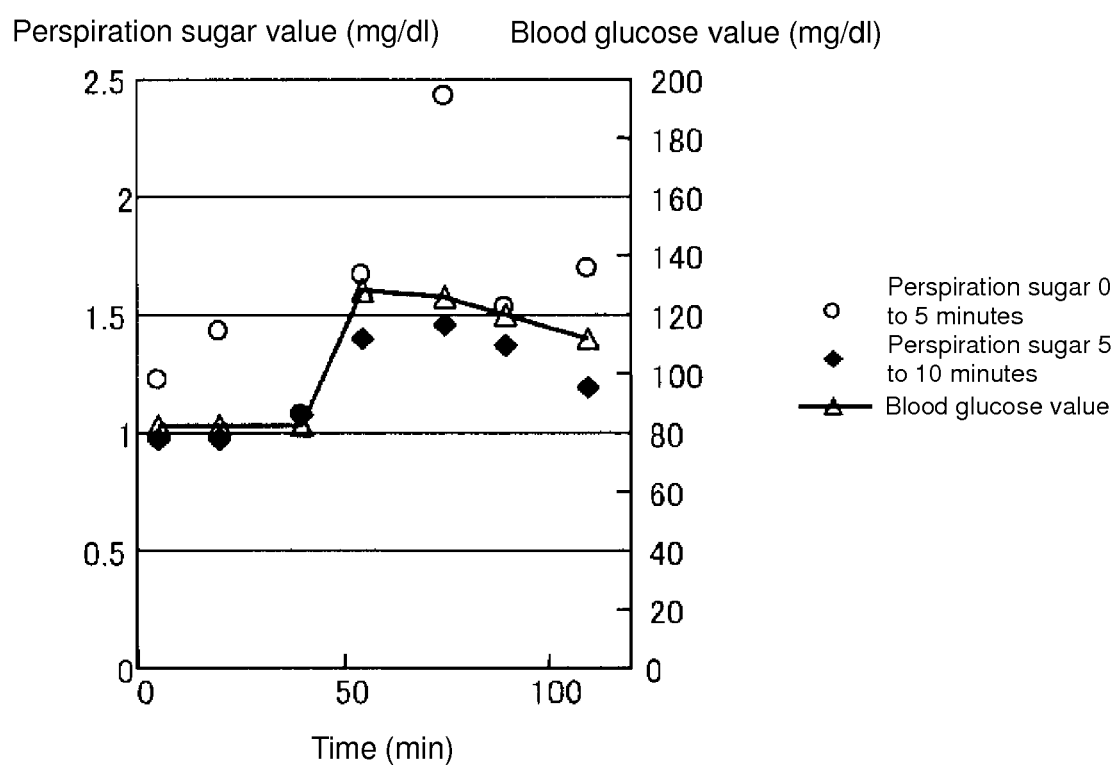
FIG. 25 is a view showing a sample of change in concentration of the perspiration sugar value obtained from the perspiration from after 0 minutes from the perspiration acceleration until elapse of five minutes, the perspiration sugar value obtained from the perspiration from after elapse of five minutes to elapse of ten minutes, and the blood glucose value by repeating perspiration acceleration with respect to the same subject.
Figure 26:
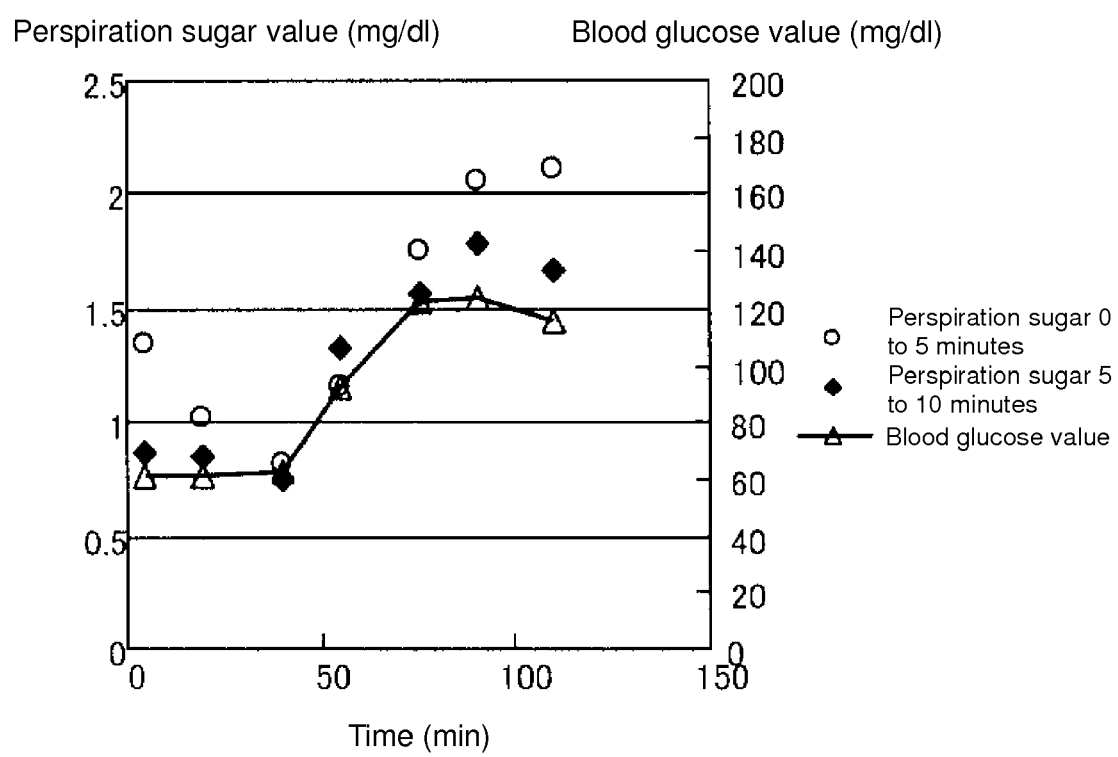
FIG. 26 is a view showing a sample of change in concentration of the perspiration sugar value obtained from the perspiration from after 0 minutes from the perspiration acceleration until elapse of five minutes, the perspiration sugar value obtained from the perspiration from after elapse of five minutes to elapse of ten minutes, and the blood glucose value by repeating perspiration acceleration with respect to the same subject.

It is verified from the samples shown in FIG. 24 to FIG. 26 that the opening from the change in concentration of the blood glucose value is greater and the correlation is not as found in the change in concentration of the concentration of the sugar in the perspiration (hereinafter referred to as perspiration sugar value) obtained from the perspiration after 0 minutes immediately after the perspiration acceleration until elapse of five minutes than in the change in concentration of the perspiration sugar value obtained from the perspiration from after elapse of five minutes until elapse of ten minutes after the perspiration acceleration. The elapsed time detecting portion 3905 has a configuration to detect that the elapsed time from the start of the measurement computation operation in the measurement computation device 30 is the predetermined time using the timer 3903, where the predetermined time is preferably five minutes assuming the start of the measurement computation operation is the completion of the perspiration acceleration. That is, the elapsed time detecting portion 3905 detects elapse of a predetermined time (e.g., five minutes) after the perspiration acceleration.

The behaviors of the component concentration in the blood and the component concentration in the perspiration are known to be substantially proportional. The converting portion 3909 stores a coefficient $\gamma$ as a coefficient defined in advance, and converts the concentration B of the sugar (glucose) serving as the first component in the perspiration input from the concentration acquiring portion 3907 to the sugar concentration A in the blood using the following equation (1):

$$A = \gamma B \qquad \text{Equation (1)}$$

The coefficient $\gamma$ may be obtained at the time of computation and the like by the conversion computation unit 309 in place of that stored in advance. For instance, the coefficient $\gamma$ may be determined by the conversion computation unit 309 from the concentration obtained by measuring the perspiration sugar value and the blood glucose value a plurality of times when the blood glucose value is relatively stable such as at the time of an empty stomach. Furthermore, the coefficient $\gamma$ may be determined from the concentration obtained by measuring the perspiration sugar value and the blood glucose value once at the time of an empty stomach.

Figure 9:
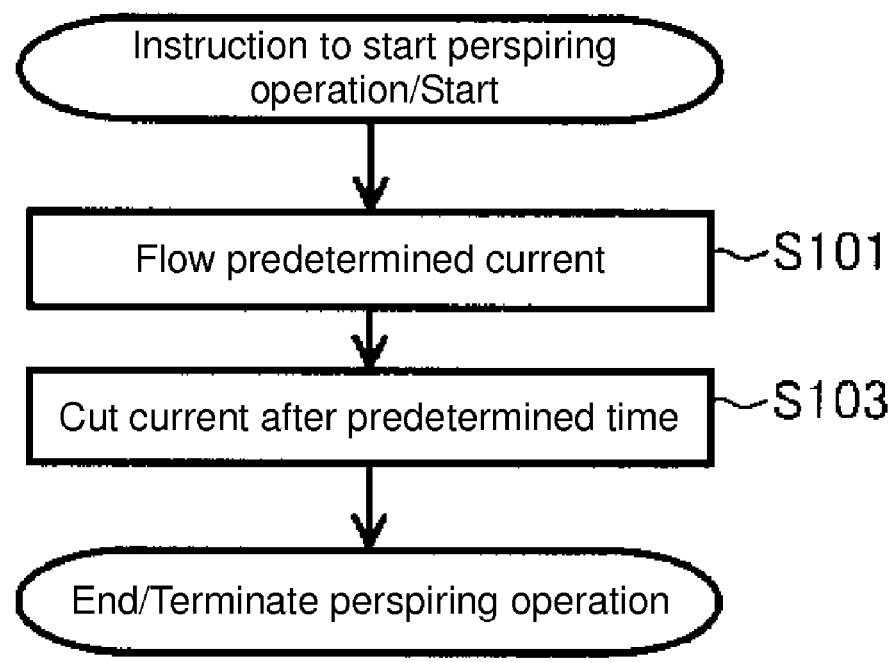
FIG. 9 is a flowchart showing a flow of the perspiring operation in the perspiration device according to a preferred embodiment of the present invention.
Figure 10:
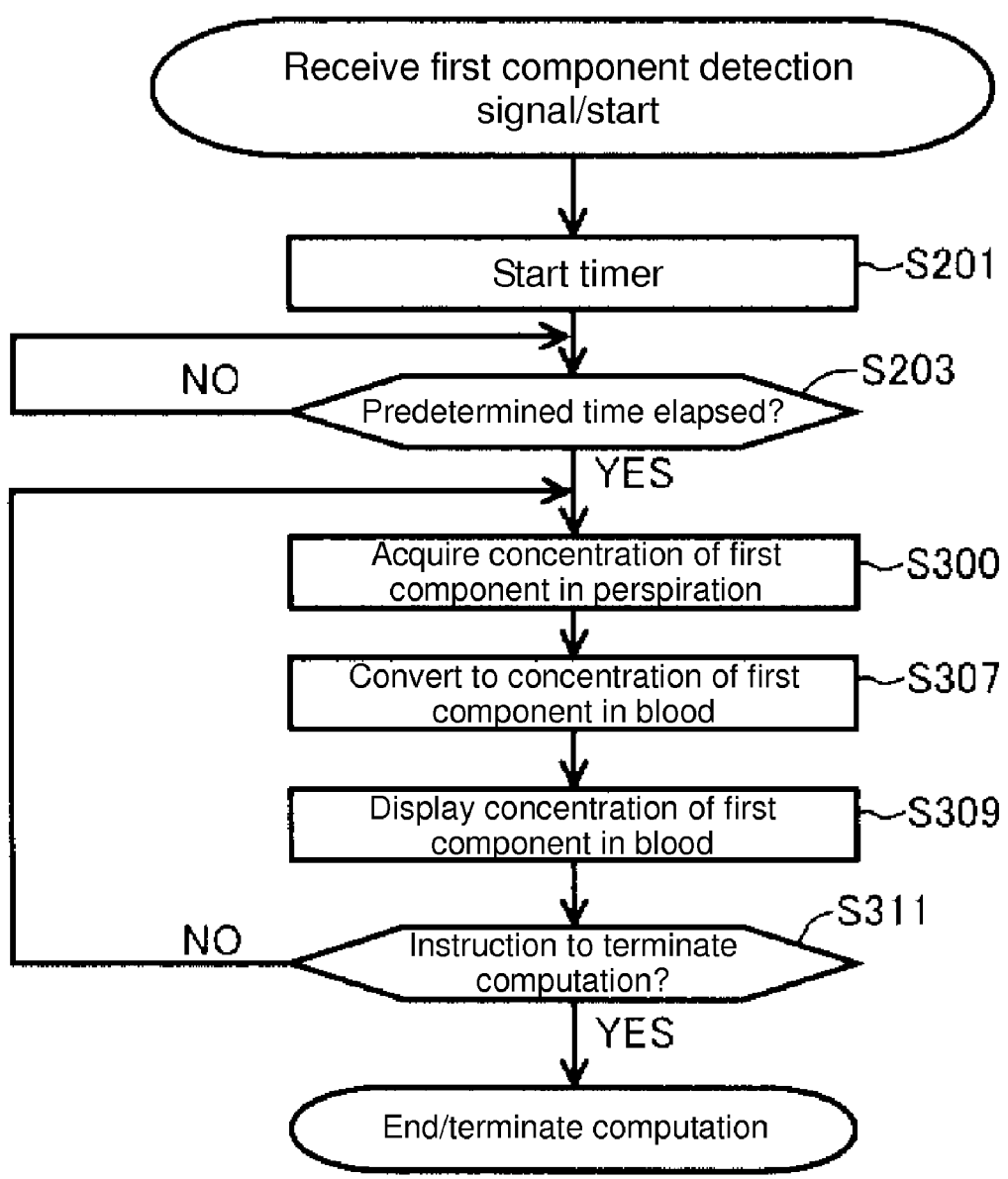
FIG. 10 is a flowchart showing a flow of the measurement computation operation in the measurement computation device according to a first preferred embodiment of the present invention.

A process flow in the measurement device 1 will now be described. FIG. 9 is a flowchart showing a flow of the perspiring operation in the perspiration device 10. FIG. 10 is a flowchart showing a flow of the measurement computation operation in the measurement computation device 30 according to the first preferred embodiment. The processes shown in the flowcharts are respectively implemented when the control circuit 15, 35 execute a predetermined computation program, and control each unit shown in FIGS. 2A, 2B, 3A, and 3B to exhibit the functions shown in FIGS. 6, 7, and 8.

First, the perspiring operation shown in FIG. 9 starts when the sponge 41 with the solution containing the perspiration accelerator such as the pilocarpine solution is attached to the medical agent region 12A, the introducing electrode 11 is attached so as to contact the sponge 41, and then the operation to start the perspiring operation is carried out with the operation unit after attaching the perspiration device 10 to the measurement site using the belt 2A so that the sponge 41 contacts the skin 100. When the input of the operation signal from the operation unit is accepted by the operation input unit 101, the control unit 103 performs a process to generate the current for flowing a predetermined DC current from the introducing power 11 to the reference electrode 13 at the current generation unit 103, and flows a predetermined current between the electrodes (step S101). After elapse of a predetermined time from the start of the perspiring operation is detected or when accepting the input of the operation signal indicating the operation of operation termination at the operation input unit 101 after elapse of a predetermined time, the control unit 103 terminates the generation of the current at the current generation unit 105, and cuts the current flowing between the electrodes (step S103).

The perspiring operation in the perspiration device 10 is then terminated. Thereafter, the subject resolves the attachment state of the perspiration device 10 and detaches the sponge 41 from the skin 100, which is the measurement site, and cleans the skin 100. The subject then attaches the measurement computation device 30 at the same position using the belt 2B. The sponge 43 of the perspiration collection region 32 collects the perspiration perspired from the skin 100 to which the pilocarpine solution is infiltrated.

The measurement computation operation in the measurement computation device 30 according to the first preferred embodiment may be started when the instruction to start the measurement computation operation is made at the operation unit with the measurement computation device 30 attached to the measurement site or attached for a constant time and detached after the perspiration is collected by the sponge 43, may be started when detected that the collected perspiration amount reached a predetermined amount by the liquid sensor 38 shown in FIG. 5, or may be started when the detection signal corresponding to the detection amount of the first component is input from the first component detection unit 303 to the concentration calculation unit 307. The measurement computation operation in the measurement computation device 30 shown in FIG. 10 is started when the detection signal corresponding to the detection amount of the first component is input from the first component detection unit 303 to the concentration calculation unit 307, and terminated when the operation signal for terminating the computation is input from the operation unit.

First, the concentration calculation unit 307 calculates the concentration of the first component in the perspiration from the detection signal when receiving the detection signal corresponding to the detection amount of the first component from the first component detection unit 303, and stores the same in the concentration storage portion 3901. This process is performed at a constant interval until the conversion computation operation is terminated.

With reference to FIG. 10, when the detection signal corresponding to the detection amount of the first component is input from the first component detection unit 303, the timing at the timer 3903 starts (step S201). When elapse of a predetermined time is detected at the elapsed time detecting portion 3905 (YES in step S203), the concentration acquiring portion 3907 acquires the concentration of the first component in the perspiration of after the relevant time point (step S300). In the converting portion 3909, the concentration of the first component in the perspiration is converted to the concentration of the first component in the blood with equation (1) (step S307), and input to the display unit 311. At the display unit 311, a process of displaying the computation result on the display 37 is executed, and the concentration of the first component in the blood obtained in step S307 is displayed (step S309).

The processes of steps S300 to S309 are repeated at a predetermined interval until the operation of terminating the conversion computation operation is made, and the concentration of the first component in the blood is displayed at a predetermined interval. When the operation signal for terminating the conversion computation operation is input from the operation unit (YES in step S311), the conversion computation operation in the measurement computation device 30 is terminated.

As shown with the samples of FIG. 19 to FIG. 26, the changes between the concentration of the first component in the perspiration and the concentration of the first component in the blood are not correlated at the initial stage after forced perspiration. Furthermore, it is verified that the beginning of perspiration is about 0 minutes after the perspiration acceleration until elapse of five minutes from the samples of FIG. 24 to FIG. 26. In the measurement conversion device 30 according to the present preferred embodiment, a predetermined time (e.g., five minutes) defined as the time at the beginning of perspiration is stored in advance, and the concentration of the first component in the perspiration of after elapse of such time is acquired by the concentration acquiring portion 3907 and used in the conversion process in the converting portion 3909. In other words, the concentration of the first component in the perspiration until elapse of a predetermined time defined in advance is not acquired by the concentration acquiring portion 3907, and not used in the conversion process in the converting portion 3909. Thus, the concentration of the first component in the perspiration while the change in concentration is not correlated with the concentration of the first component in the blood is not used to calculate the concentration of the first component in the blood in the conversion process of the converting portion 3909, and the concentration of the first component in the perspiration of after elapse of a predetermined time, at which correlation is found, is used in the calculation. As a result, the concentration of the first component in the blood can be measured at high accuracy.

The above-described configuration and the process are one specific example, and are not limited to such configuration and process. The concentration of the first component in the perspiration may be calculated in the concentration calculation unit 307 after elapse of a predetermined time is detected by the elapsed time detecting portion 3905. The concentration of the first component in the perspiration may be converted to the concentration of the first component in the blood in the converting portion 3909 before elapse of a predetermined time is detected, and the concentration of the first component in the blood after elapse of a predetermined time is detected may be displayed on the display unit 311.

Second Preferred Embodiment

A case of using the rate of change of the concentration of the first component in the perspiration will be described as a second preferred embodiment of the measurement computation device 30 for measuring the concentration of the first component in the blood.

The mechanical configuration and the function configuration of the measurement computation device 30 according to the second preferred embodiment are similar to those shown in FIGS. 3A and 3B, and FIG. 7.

Figure 11:
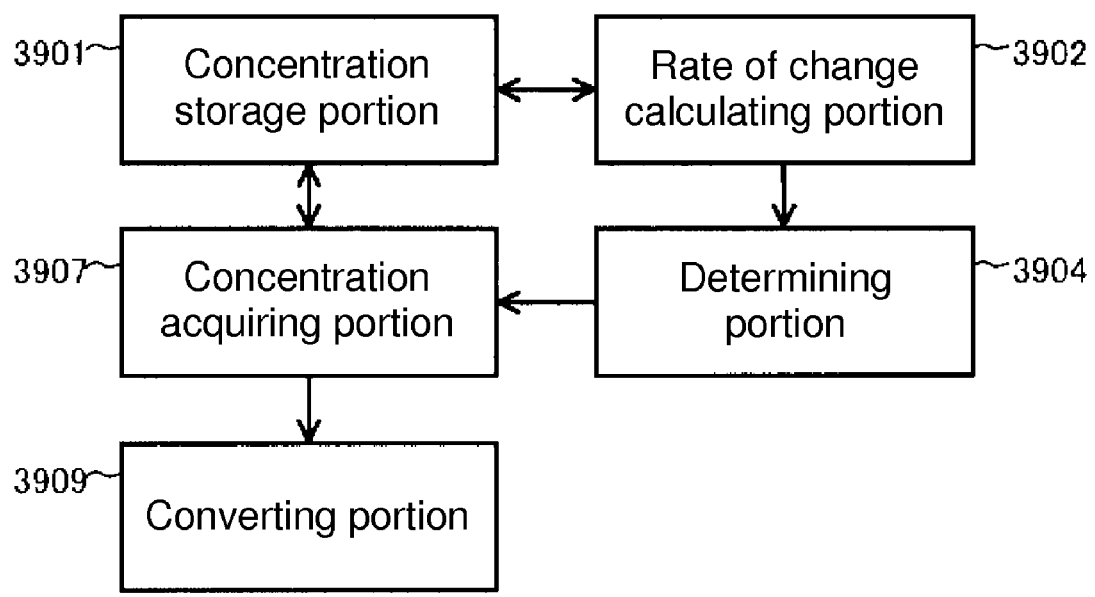
FIG. 11 is a block diagram showing a specific example of the detailed configuration of the conversion computation unit of the measurement computation device according to a second preferred embodiment of the present invention.

FIG. 11 is a block diagram showing a specific example of the detailed configuration of the conversion computation unit 309 of the measurement computation device 30 according to the second preferred embodiment. With reference to FIG. 11, in the second preferred embodiment, a rate of change calculating portion 3902 and a determining portion 3904 are arranged in place of the timer 3903 and the elapsed time detecting portion 3905 of the configuration of the conversion computation unit 309 shown in FIG. 8.

The rate of change calculating portion 3902 calculates the rate of change Pn of the concentration from the concentration $A_n$ of the first component in the perspiration obtained from the $N^{th}$ measurement result and the concentration $A_{n+1}$ of the first component in the perspiration obtained from the $N+1^{th}$ measurement result stored in the concentration storage portion 3901, and inputs the same to the determining portion 3904. The method of calculating the rate of change Pn in the rate of change calculating portion 3902 is not limited to a specific method, and the rate of change can be calculated using the following equations (2) and (3).

$$Pn=(A_n-A_{n+1})/A_{n+1} \hspace{2em} \text{Equation (2)}$$

$$Pn=(A_n-A_{n+1})/(A_{n+1}-\alpha) \hspace{2em} \text{Equation (3) ($\alpha$ is a constant defined in advance).}$$

The method of calculating the rate of change Pn in the rate of change calculating portion 3902 also includes a method of calculating a derivative value of the concentration of the first component in the perspiration.

The rate of change calculating portion 3902 sequentially calculates the rate of change of the concentration from the concentration of the first component in the perspiration stored in the concentration storage portion 3901, and inputs the same to the determining portion 3904. In the determining portion 3904, the input rate of change is compared with the threshold value stored in advance to determine whether it is smaller than or equal to the threshold value. The threshold value is not limited to a specific value. The determining portion 3904 determines whether or not the rate of change from the previous concentration is smaller than or equal to 10% using 10% (0.1), for example, for the threshold value. If it is determined that the calculated rate of change is smaller than or equal to the threshold value, a signal indicating the same is input to the concentration acquiring portion 3907, the subsequent (N) concentrations are acquired from the concentration storage portion 3901 and input to the converting portion 3909.

Figure 12:
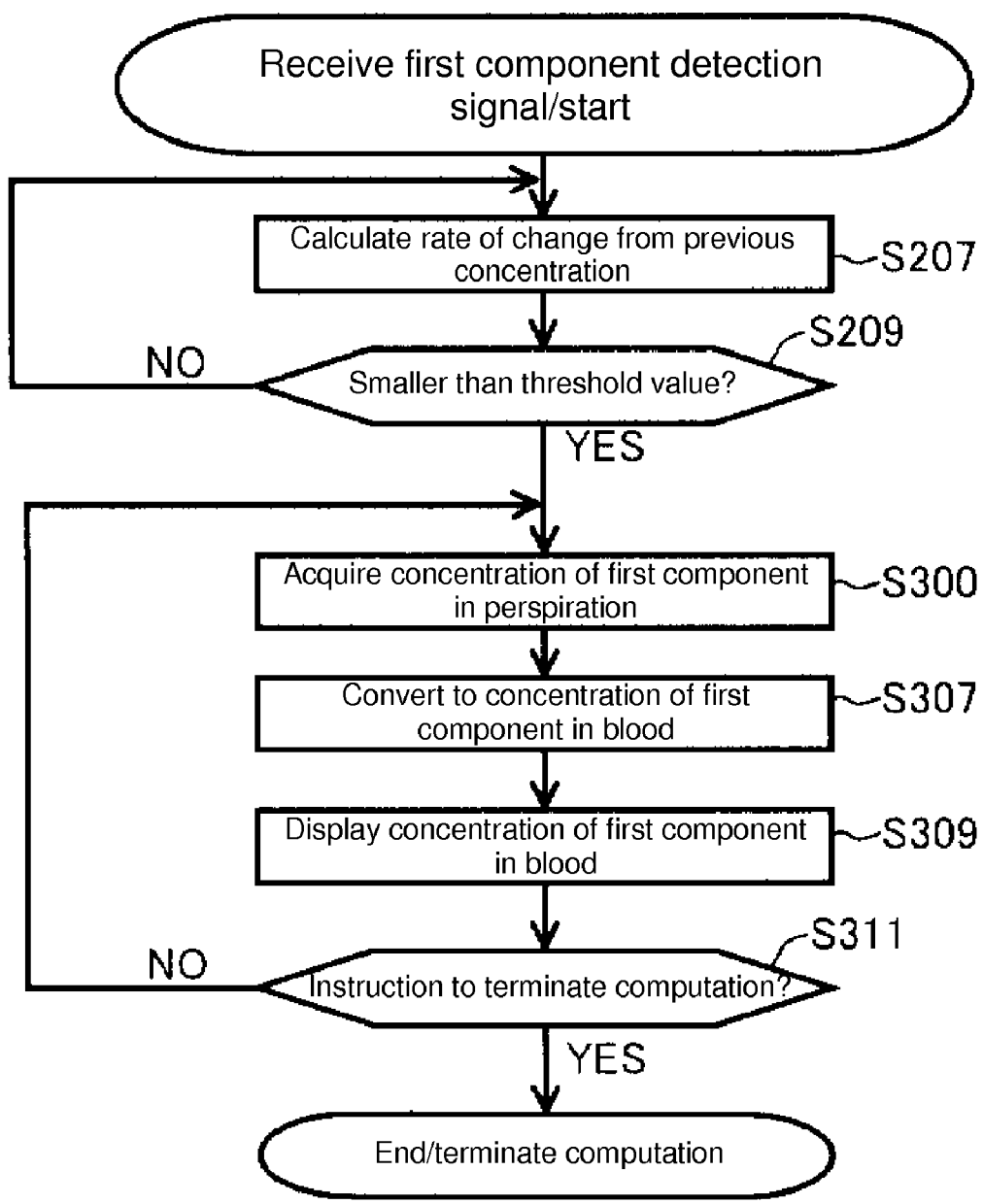
FIG. 12 is a flowchart showing a flow of the measurement computation operation in the measurement computation device according to the second preferred embodiment of the present invention.

FIG. 12 is a flowchart showing a flow of the measurement computation operation in the measurement computation device 30 according to the second preferred embodiment. The processes shown in the flowchart of FIG. 12 are also implemented when the control circuit 35 executes a predetermined computation program, and controls each unit shown in FIGS. 3A, 3B to exhibit the functions shown in FIGS. 7, 11.

First, when receiving the detection signal corresponding to the detection amount of the first component from the first component detection unit 303, the concentration calculation unit 307 calculates the concentration of the first component in the perspiration from the detection signal, and stores the same in the concentration storage portion 3901. This process is performed at a constant interval until the conversion computation operation is terminated.

With reference to FIG. 12, when the detection signal corresponding to the detection amount of the first component is input from the first component detection unit 303, the rate of change calculating portion 3902 calculates the rate of change using equation (2) and equation (3) from the concentration of the first component in the perspiration obtained from the measurement result of the previous time and the concentration of the first component in the perspiration obtained from the measurement result of this time (step S207), and inputs the same to the determining portion 3904. The computation of step S207 is repeated until it is determined that the rate of change calculated in step SS207 is smaller than or equal to the threshold value (e.g., 10%) by the determining portion 3904. If determined as such (YES in step S209), the concentration acquiring portion 3907 acquires the concentration of the first component in the perspiration after the relevant time point (step S300). In the converting portion 3909, the concentration of the first component in the perspiration is converted to the concentration of the first component in the blood with equation (1) (step S307), and input to the display unit 311. In the display unit 311, a process of displaying the computation result on the display 37 is executed, and the concentration of the first component in the blood obtained in step S307 is displayed (step S309).

The processes of steps S300 to S309 are repeated at a predetermined interval until the operation of terminating the conversion computation operation is made, and the concentration of the first component in the blood is displayed at a predetermined interval. When the operation signal for terminating the conversion computation operation is input from the operation unit (YES in step S311), the conversion computation operation in the measurement computation device 30 is terminated.

As shown with the samples of FIG. 19 to FIG. 26, the changes between the concentration of the first component in the perspiration and the concentration of the first component in the blood are not correlated at the initial stage after forced perspiration, and the concentration of the first component in the perspiration rapidly lowers greatly in such period than in the period after the beginning. In the measurement conversion device 30 according to the present preferred embodiment, a rate of change of the concentration of the first component in the perspiration is calculated, and the concentration of the first component in the perspiration of after the rate of change becomes smaller than or equal to the threshold value is acquired and used in the conversion process of the converting portion 3909. In other words, the concentration of the first component in the perspiration at the beginning of perspiration, in which the concentration of the first component in the perspiration rapidly changes, is not acquired by the concentration acquiring portion 3907, and not used in the conversion process of the converting portion 3909. Thus, the concentration of the first component in the perspiration while the change in concentration is not correlated with the concentration of the first component in the blood is not used to calculate the concentration of the first component in the blood in the conversion process of the converting portion 3909, and the concentration of the first component in the perspiration of after elapse of a predetermined time, at which time correlation is found, is used in the calculation. As a result, the concentration of the first component in the blood can be measured at high accuracy. Furthermore, the timer 3903 shown in the first preferred embodiment is not necessary since the beginning of perspiration is detected using the rate of change of the concentration of the first component in the perspiration.

The above-described configuration and the process are one specific example, and are not limited to such configuration and process. Similar to the first preferred embodiment, the concentration of the first component in the perspiration may be converted to the concentration of the first component in the blood in the converting portion 3909 before the detection that the rate of change of the concentration of the first component in the perspiration is smaller than or equal to the threshold value, and the concentration of the first component in the blood after the detection may be displayed on the display unit 311.

Third Preferred Embodiment

A case of using the rate of change of the concentration of the second component in the perspiration other than the first component will be described as a third preferred embodiment of the measurement computation device 30 for measuring the concentration of the first component in the blood.

Figure 13A:
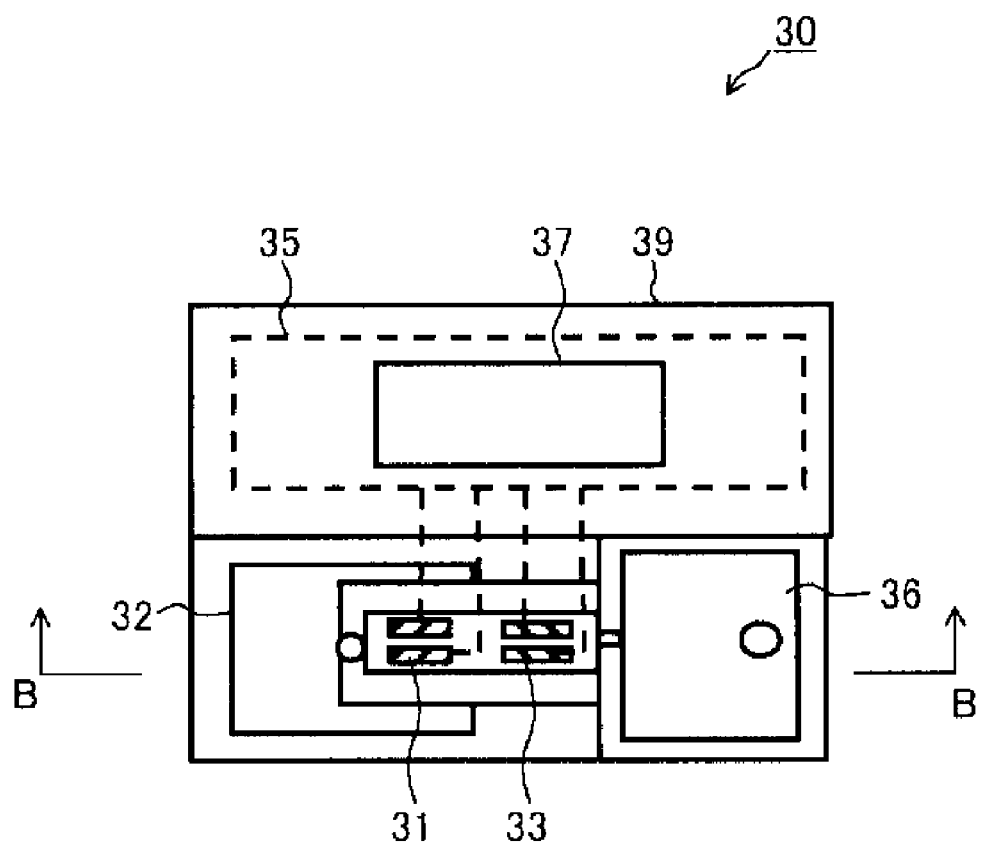
FIG. 13A is a view of the mechanical configuration of the measurement computation device according to a third preferred embodiment of the present invention seen from the front surface.
Figure 13B:
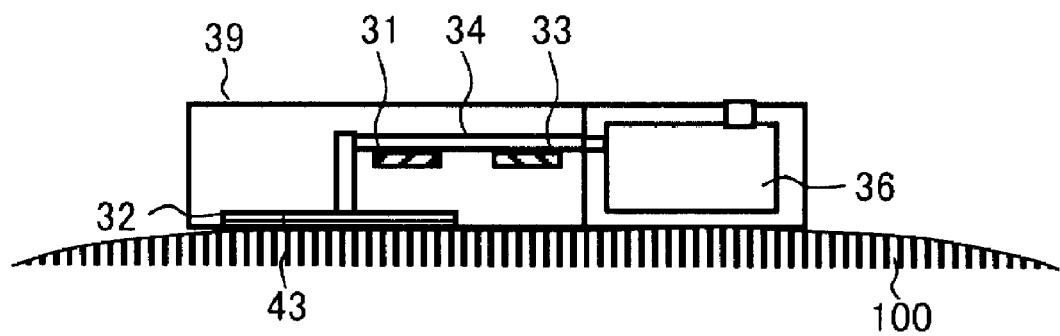
FIG. 13B is a view showing the cross-section at the position shown with an arrow B in FIG. 13A of the mechanical configuration of the measurement computation device according to the third preferred embodiment of the present invention.

FIGS. 13A, 13B are views showing the specific example of the mechanical configuration of the measurement computation device 30 according to the third preferred embodiment. With reference to FIG. 13A, the measurement computation device 30 according to the third preferred embodiment includes, inside the housing 39, the second component detector 33 arranged to detect the second component in the perspiration connected to the control circuit 35, in addition to the configuration shown in FIG. 3A. FIG. 13B is a schematic view of the mechanical configuration of the cross-section of the measurement computation device 30 according to the third preferred embodiment at the position shown with an arrow B in FIG. 13A. With reference to FIG. 13B, the perspiration collected by the perspiration collection region 32 is conveyed to the discarding liquid storage unit 36 through the first component detector 31 and the second component detector 33 by the conveyance path 34.

Figure 14:
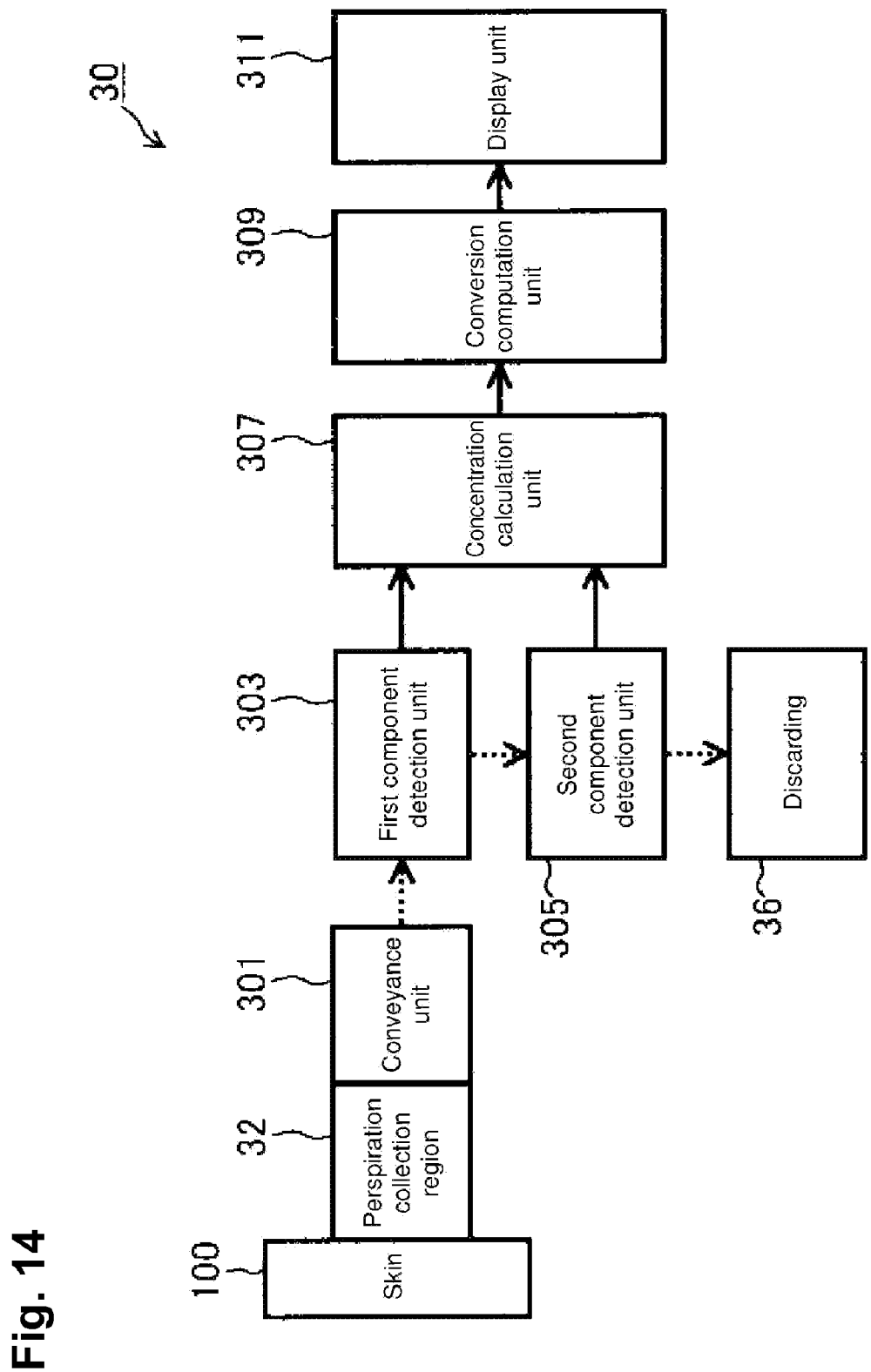
FIG. 14 is a block diagram showing a specific example of the functional configuration of the measurement computation device according to the third preferred embodiment of the present invention.

FIG. 14 is a block diagram showing a specific example of the function configuration of the measurement computation device 30 according to the third preferred embodiment. The function of the measurement computation device 30 according to the third preferred embodiment includes a second component detection unit 305 arranged to detect the second component in the perspiration, in addition to the functions shown in FIG. 7. The second component detection unit 305 mainly includes the second component detector 33, and detects the second component using the second component detector 33 from the perspiration conveyed by the conveyance unit 301, and inputs the detection signal corresponding to the detection amount to the concentration calculation unit 307. The concentration calculation unit 307 calculates the concentration of the first component and the concentration of the second component in the perspiration based on the detection signals from the first component detection unit 303 and the second component detection unit 305. The signal indicating the calculated concentration is input to the conversion computation unit 309.

The second component is a component in the perspiration other than the first component, and preferably corresponds to a component in which the change in concentration in the perspiration and the change in concentration in the blood are not related, or the relevance is lower than a predetermined correlation coefficient. If the first component is sugar (glucose), the perspiration sugar value changes in correlation with change in the blood glucose value. The blood glucose value rapidly changes when a great amount of sugar is ingested such as in a meal. Thus, when the change in blood glucose value is rapid, the perspiration sugar also rapidly changes following thereto. If the blood glucose value and the perspiration sugar value rapidly change by ingestion of sugar, whether the change in perspiration sugar value is by ingestion of sugar or by the beginning of perspiration may not be discriminated. Thus, as shown in the second preferred embodiment, if the blood glucose value and the perspiration sugar value rapidly change, it is preferable to measure the component that is less likely to change due to a meal other than sugar, that is, the second component in the perspiration that does not follow the change in the blood glucose value, and detect the beginning of perspiration using the rate of change thereof rather than detecting the beginning of perspiration using the rate of change of the perspiration sugar value. The other component in the perspiration other than sugar is also known to transition to high concentration at the beginning of perspiration than after the beginning of perspiration, and includes component in the perspiration that does not change following the blood glucose value even when a great amount of sugar is ingested, that is, component in the perspiration that is not influenced by change in concentration of the blood glucose value. The second component that satisfies such condition specifically includes, if the first component is sugar, calcium and potassium and amino acids such as lysine, glutamine, asparagine acid, and glutamic acid.

Figure 15:
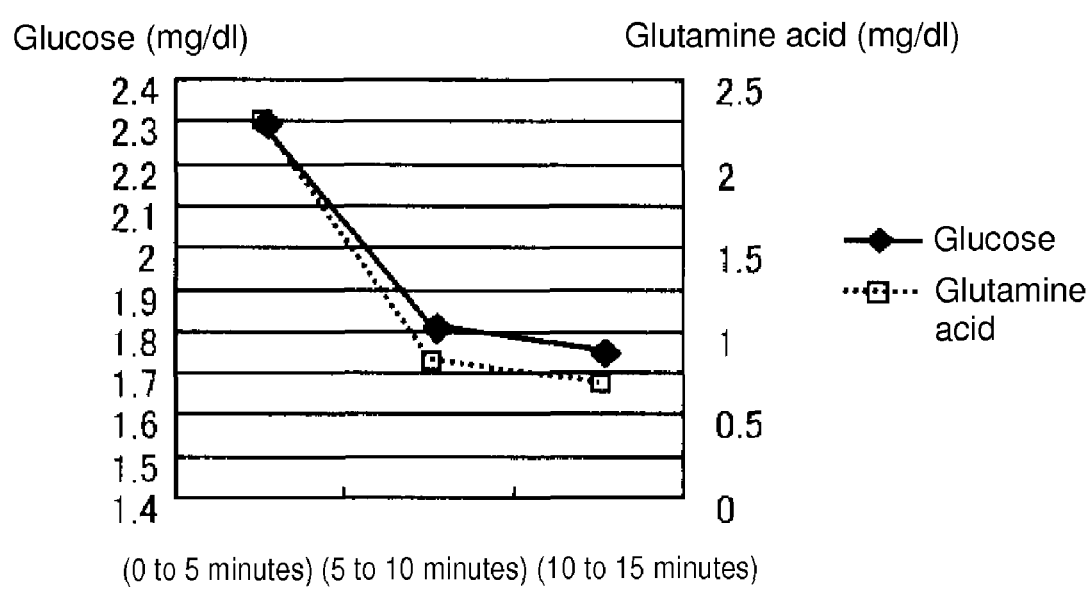
FIG. 15 is a view showing a sample obtained by measuring a change in the concentration of the component when the blood glucose value is constant.
Figure 16:
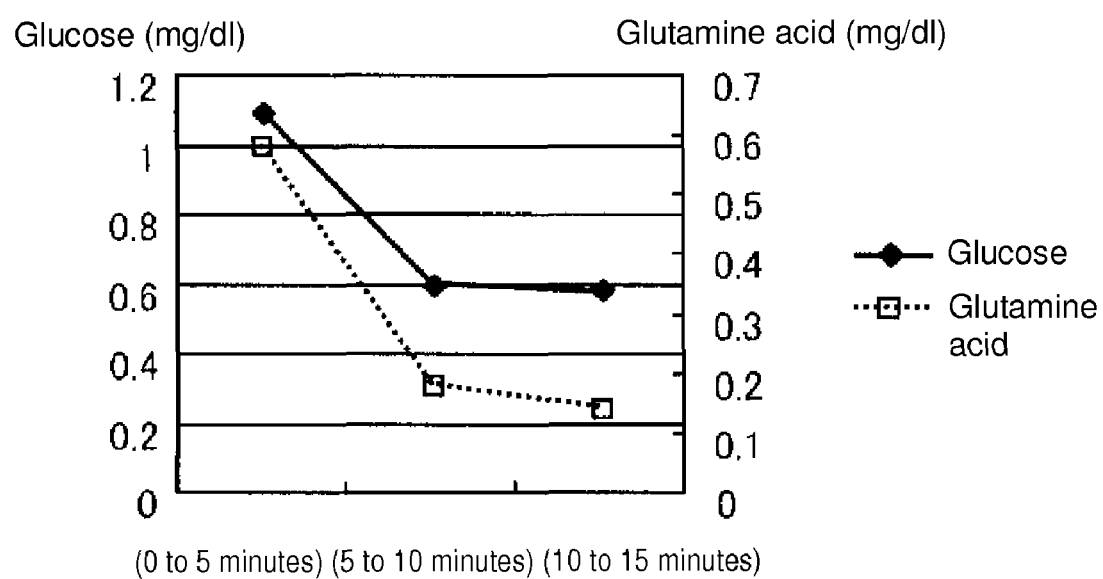
FIG. 16 is a view showing a sample obtained by measuring a change in the concentration of the component when the blood glucose value is constant.

FIG. 15 and FIG. 16 show two samples obtained by measuring the change in concentration of the component in the perspiration when the blood glucose value is constant. Here, the concentration of the sugar (glucose) and the concentration of the glutamic acid are measured for every predetermined time as components in the perspiration to obtain the samples. It can be seen from FIG. 15 and FIG. 16 that the sugar, which is the first component in the perspiration, tends to be high concentration at the beginning of perspiration than after the beginning of perspiration although the blood glucose value is constant. In this case, the glutamine acid also indicates the same tendency, and is subjected to the same influence as the glucose.

Figure 17:
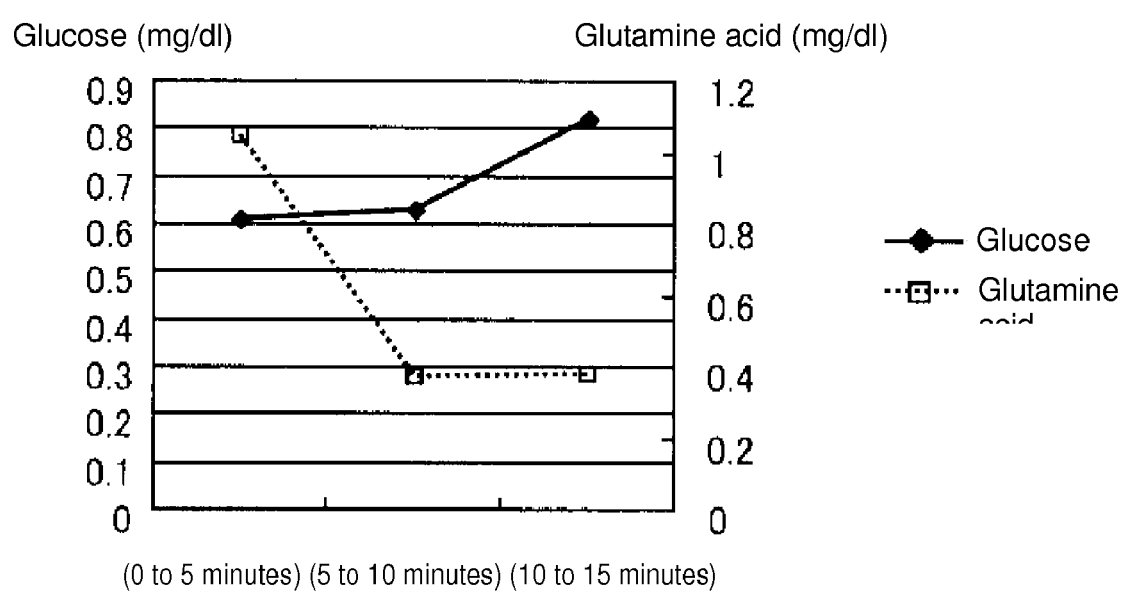
FIG. 17 shows samples obtained by rapidly raising the blood glucose value, and measuring a change in the concentration of the component in the perspiration.

FIG. 17 shows samples obtained by rapidly raising the blood glucose value by ingesting a great amount of sugar, and the like, and measuring the change in concentration of the component in the perspiration. With reference to FIG. 17, it is found that the concentration at the beginning of perspiration of the perspiration sugar value in this case is not high compared to the changes shown in FIG. 15 and FIG. 16. This is because the sugar in the perspiration is subjected to a change in the blood glucose value from the beginning of perspiration. However, the glutamine acid in the perspiration that is not subjected to a change in blood glucose value indicates high concentration at the beginning of perspiration than after the beginning of perspiration, similar to the changes shown in FIG. 15 and FIG. 16.

In the present preferred embodiment, the second component is assumed to be glutamic acid. Furthermore, in the third preferred embodiment, the second component detector 33 is configured to use the enzyme electrode method, and has a configuration in which L-glutamic acid glutamate oxidase and an electrode are combined to detect the glutamic acid as the second component The detailed configuration of the conversion computation unit 309 of the measurement computation device 30 according to the third preferred embodiment is similar to the detailed configuration of the conversion computation unit 309 of the measurement computation device 30 according to the second preferred embodiment shown in FIG. 11. In the third preferred embodiment, the concentration storage portion 3901 stores the concentration of the first component and the concentration of the second component sequentially calculated by the concentration calculation unit 307. The rate of change calculating portion 3902 calculates the rate of change Qn of the concentration from the concentration $B_n$ of the second component in the perspiration obtained from the $N^{th}$ measurement result and the concentration $B_{n-1}$ of the first component in the perspiration obtained from the $N+1^{th}$ measurement result stored in the concentration storage portion 3901, and inputs the same to the determining portion 3904. The calculation method of the rate of change Qn in the rate of change calculating portion 3902 is not limited to a specific method, and the rate of change can be calculated using the following equation (4) and equation (5).

$$Qn = (B_n - B_{n+1})/B_{n+1} \qquad \text{Equation (4)}$$

$$Qn = (B_n - B_{n+1})/(B_{n+1}\beta) \qquad \text{Equation (5) ($\beta$ is a constant defined in advance).}$$

The rate of change calculating portion 3902 sequentially calculates the rate of change of the concentration from the concentration of the second component in the perspiration stored in the concentration storage portion 3901, and inputs the same to the determining portion 3904. In the determining portion 3904, the input rate of change is compared with the threshold value stored in advance to determine whether or not smaller than or equal to the threshold value. The threshold value here is not limited to a specific value. The determining portion 3904 determines whether or not the rate of change from the previous concentration is smaller than or equal to 10% using 10% (0.1) and the like for the threshold value. If it is determined that the calculated rate of change is smaller than or equal to the threshold value, a signal indicating the same is input to the concentration acquiring portion 3907, and the concentration of the first component after (N) is acquired from the concentration storage portion 3901 and input to the converting portion 3909.

Figure 18:
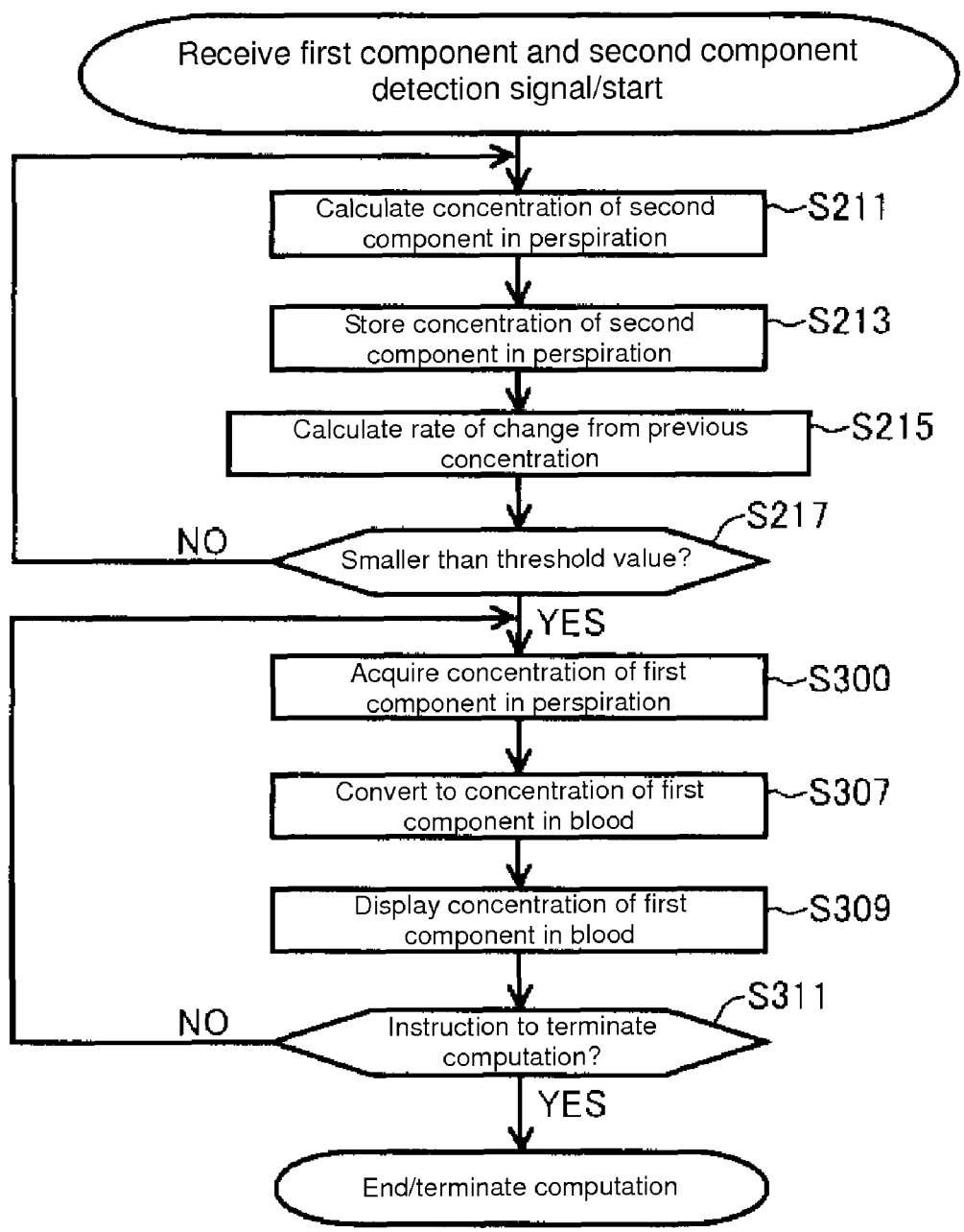
FIG. 18 is a flowchart showing a flow of the measurement computation operation in the measurement computation device according to the third preferred embodiment of the present invention.
Figure 19:
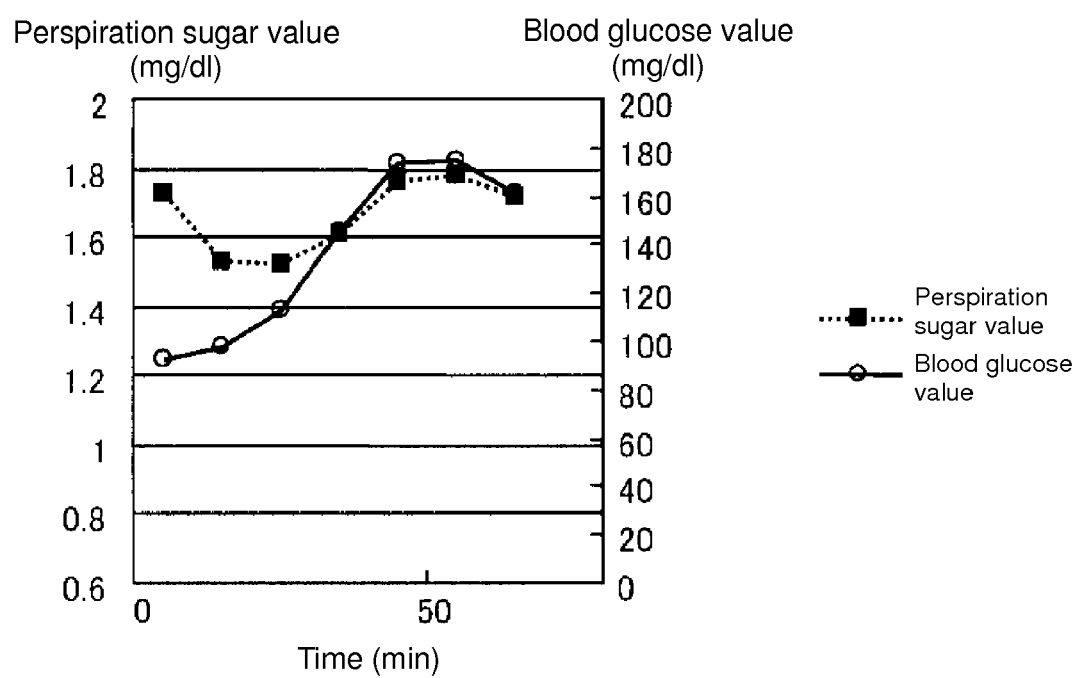
FIG. 19 is a view showing a sample of change in concentration of the perspiration sugar value and the blood glucose value when the perspiration is continuously collected after the perspiration acceleration of one time.
Figure 20:
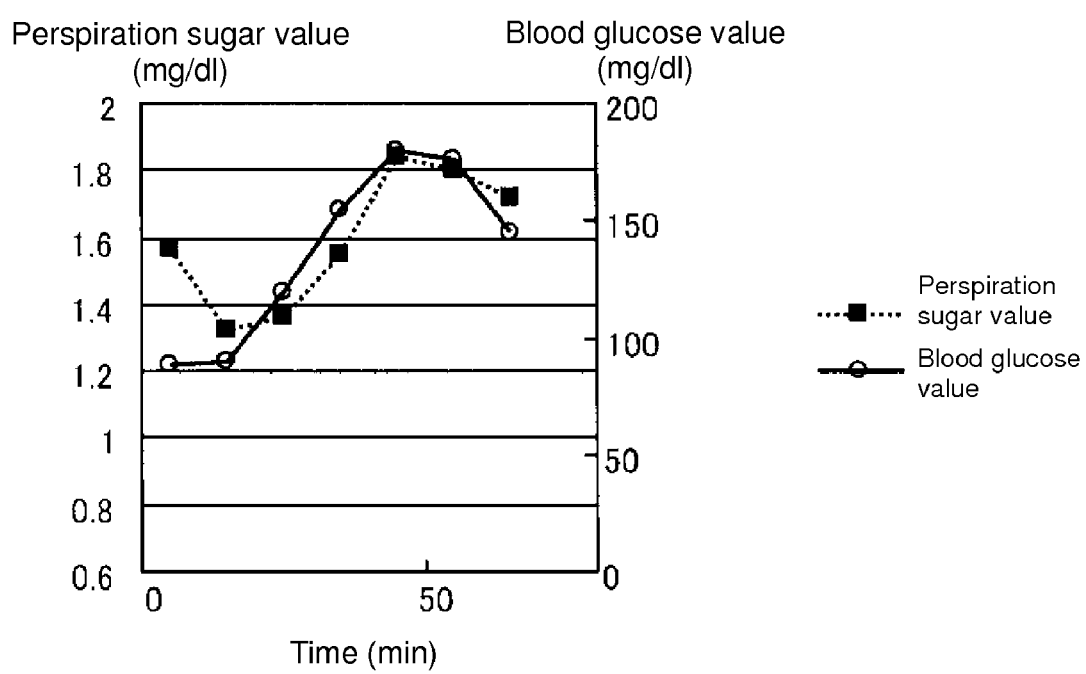
FIG. 20 is a view showing a sample of change in concentration of the perspiration sugar value and the blood glucose value when the perspiration is continuously collected after the perspiration acceleration of one time.
Figure 21:
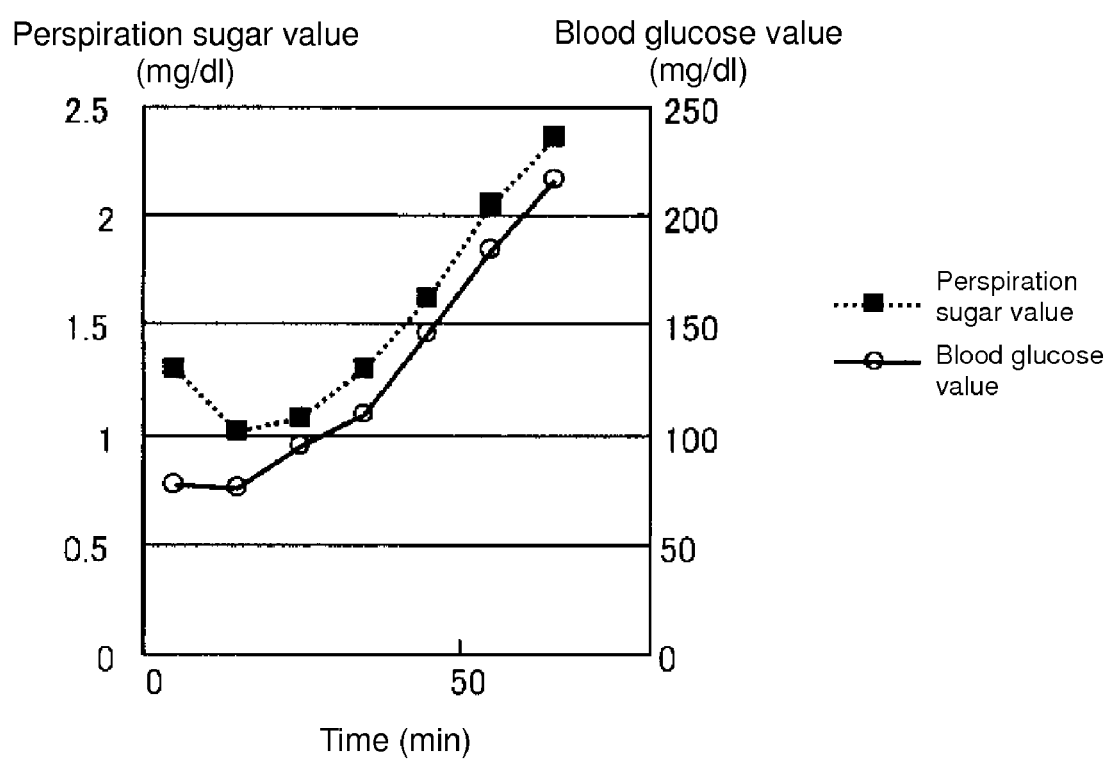
FIG. 21 is a view showing a sample of change in concentration of the perspiration sugar value and the blood glucose value when the perspiration is continuously collected after the perspiration acceleration of one time.
Figure 22:
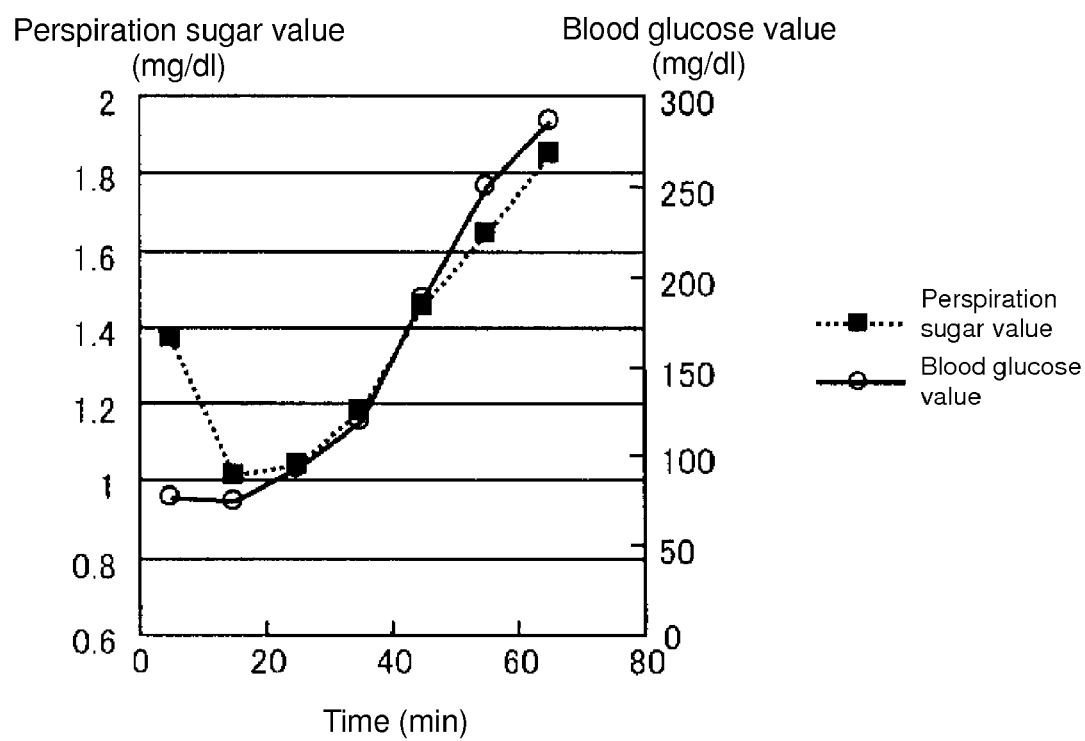
FIG. 22 is a view showing a sample of change in concentration of the perspiration sugar value and the blood glucose value when the perspiration is continuously collected after the perspiration acceleration of one time.
Figure 23:
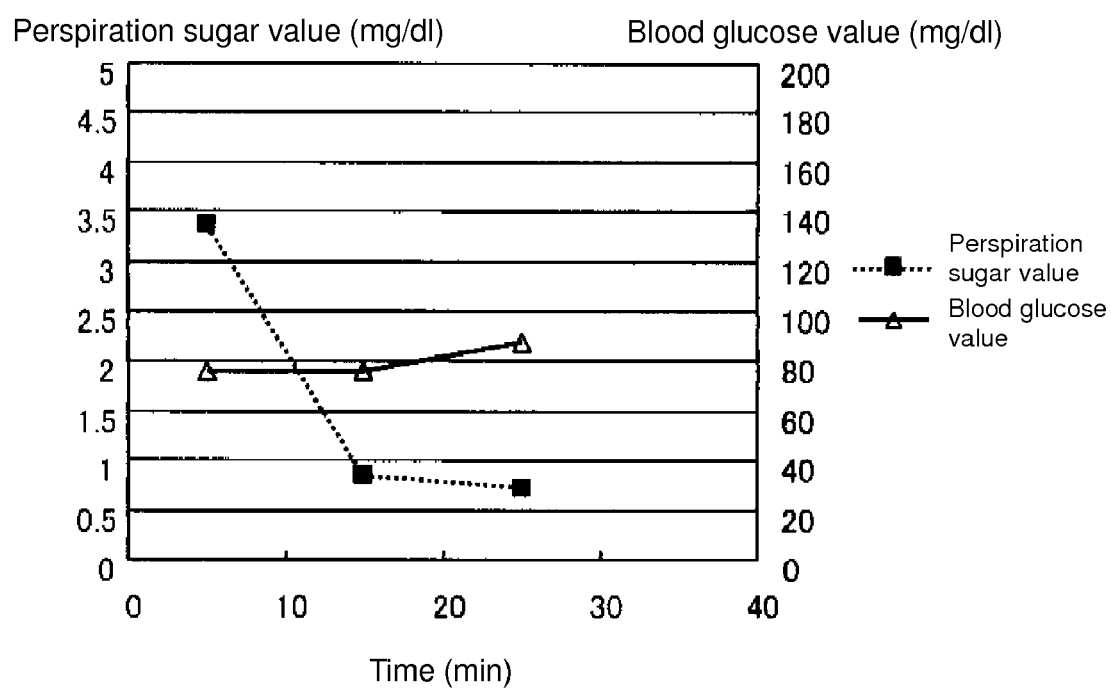
FIG. 23 is a view showing a sample obtained by performing a measurement of the perspiration sugar value and the blood glucose value after the exercise perspiration.

FIG. 18 is a flowchart showing a flow of the measurement computation operation in the measurement computation device 30 according to the third preferred embodiment. The processes shown in the flowchart of FIG. 18 are also implemented when the control circuit 35 executes a predetermined computation program, and controls each unit shown in FIGS. 3A, 3B to exhibit the functions shown in FIGS. 11, 15.

With reference to FIG. 12, the concentration calculation unit 307 calculates the concentration of the second component in the perspiration from the detection signals (step S211) when receiving the detection signal corresponding to the detection amount of the first component and the detection signal corresponding to the detection amount of the second component from the first component detection unit 303 and the second component detection unit 305, and stores the same in the concentration storage portion 3901 (step S213). Similarly, the concentration of the first component in the perspiration is also calculated from the detection signal and stored in the concentration storage portion 3901. The process of calculating the concentration of the first component is assumed to be carried out at a constant interval until the conversion computation operation is terminated.

The rate of change is calculated using equation (4) and equation (5) from the concentration of the second component in the perspiration obtained from the measurement result of the previous time and the concentration of the second component in the perspiration obtained from the measurement result of this time in the rate of change calculating portion 3902 (step S215), and input to the determining portion 3904. The computation of step S215 is repeated until it is determined that the rate of change calculated in step S215 is smaller than or equal to the threshold value (e.g., 10%) in the determining portion 3904. If determined as such (YES in step S217), the concentration acquiring portion 3907 acquires the concentration of the first component in the perspiration after the relevant time point (step S300). In the converting portion 3909, the concentration of the first component in the perspiration is converted to the concentration of the first component in the blood with equation (1) (step S307), and input to the display unit 311. At the display unit 311, a process of displaying the computation result on the display 37 is executed, and the concentration of the first component in the blood obtained in step S307 is displayed (step S309).

The processes of steps S300 to S309 are repeated at a predetermined interval until the operation of terminating the conversion computation operation is made, and the concentration of the first component in the blood is displayed at a predetermined interval. When the operation signal for terminating the conversion computation operation is input from the operation unit (YES in step S311), the conversion computation operation in the measurement computation device 30 is terminated.

In the measurement conversion device 30 according to the present preferred embodiment, the rate of change of the concentration of the second component in the perspiration that is not influenced by change in concentration of the first component in the blood is calculated, and the concentration of the first component in the perspiration after the rate of change becomes smaller than or equal to the threshold value is acquired and used in the conversion process in the converting portion 3909. In other words, the concentration of the first component in the perspiration at the beginning of perspiration, at which the concentration of the second component in the perspiration rapidly changes, is not acquired by the concentration acquiring portion 3907, and not used in the conversion process in the converting portion 3909. Thus, as shown with the samples of FIG. 17, even if the concentration of the first component in the perspiration changes with a change in the concentration of the first component in the blood, and such a change is difficult to discriminate whether by the change in concentration in the blood or by the beginning of perspiration, the beginning of perspiration can be detected using the rate of change of the concentration of the second component in the perspiration that is not influenced by the change in concentration of the first component in the blood. As a result, the concentration of the first component in the perspiration while the change in concentration is not correlated with the concentration of the first component in the blood is not used to calculate the concentration of the first component in the blood in the conversion process of the converting portion 3909, and the concentration of the first component in the perspiration after elapse of a predetermined time, when correlation is found, is used in the calculation. Thus, the concentration of the first component in the blood can be measured with high accuracy.

The above-described configurations and processes are one specific example, and are not limited to such configurations and processes. For instance, similar to the first preferred embodiment, a configuration in which the concentration of the first component in the perspiration is calculated in the concentration calculation unit 307 after it is detected that the rate of change of the concentration of the second component in the perspiration is smaller than or equal to the threshold value may be adopted. The concentration of the first component in the perspiration may be converted to the concentration of the first component in the blood in the converting portion 3909 before the detection, and the concentration of the first component in the blood maybe displayed at the display unit 311 after the detection. Furthermore, the detection of the second component and the calculation of the concentration may not be performed after the detection.

In the example described above, one second component (glutamic acid in the specific example) is used as another component of the first component, but a plurality of perspiration components may be used for the second component. For instance, if the first component is sugar, calcium and potassium and amino acids such as glutamic acid, lysine, glutamine, and asparagine acid may be used for the second component.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A blood component concentration measurement device comprising:
   a perspiration accelerating unit arranged to accelerate perspiration from a measurement site of a body;
   a first measurement unit arranged to measure a concentration in the perspiration of a first component contained in the perspiration from the measurement site;
   a detecting portion arranged to detect an elapse of a predetermined time after acceleration of the perspiration; and
   a converting portion arranged to convert the concentration in the perspiration of the first component contained in the perspiration from the measurement site after elapse of the predetermined time to concentration of the first component in blood of the body; wherein
   the detecting portion includes:
      a calculating portion arranged to calculate a rate of change of the concentration of the first component in the perspiration, and
      a determining portion arranged to compare the rate of change and a threshold value and to determine the elapse of the predetermined time when the rate of change is smaller than the threshold value.

2. The blood component concentration measurement device according to claim 1, wherein the first component is sugar.

3. A blood component concentration measurement device comprising:
   a perspiration accelerating unit arranged to accelerate perspiration from a measurement site of a body;

a first measurement unit arranged to measure a concentration in the perspiration of a first component contained in the perspiration from the measurement site;

a second measuring unit arranged to measure a concentration in the perspiration of a second component, different from the first component, contained in the perspiration from the measurement site;

a detecting portion arranged to detect an elapse of a predetermined time after acceleration of the perspiration; and a converting portion arranged to convert the concentration in the perspiration of the first component contained in the perspiration from the measurement site after elapse of the predetermined time to concentration of the first component in blood of the body; wherein the detection portion includes:
- a calculating portion arranged to calculate a rate of change of the concentration of the second component in the perspiration, and
- a determining portion arranged to compare the rate of change and a threshold value and to determine the elapse of the predetermined time when the rate of change is smaller than the threshold value.

4. The blood component concentration measurement device according to claim 3, wherein the second component is a component in which the change in concentration in the perspiration and the change in concentration in the blood are not related.

5. The blood component concentration measurement device according to claim 3, wherein the first component is sugar, and the second component is at least one of glutamic acid, lysine, glutamine, asparagine acid, calcium, and potassium.

6. A blood component measurement method performed by a blood component concentration measurement device which includes an acquiring device arranged to acquire perspiration from a measurement site, a detection device arranged to detect a component in the perspiration, and a computation device arranged to perform a computation using a value obtained from the component, the method comprising the steps of:

calculating a rate of change of concentration of a first component in the perspiration with the computation device;

detecting the first component from the perspiration with the detection device after the rate of change of concentration of the first component and a threshold value are compared and the rate of change becomes smaller than the threshold value;

calculating a concentration in the perspiration of the first component with the computation device;

converting the calculated concentration in the perspiration of the first component to a concentration of the first component in blood of a body; and executing a process of outputting the concentration in the blood of the first component with the computation device.

7. A blood component measurement method performed by a blood component concentration measurement device including an acquiring device arranged to acquire perspiration from a measurement site, a detection device arranged to detect a component in the perspiration, and a computation device arranged to perform a computation using a value obtained from the component, the method comprising the steps of:

calculating a rate of change of concentration of a first component in the perspiration with the computation device;

calculating a rate of change of concentration of a second component in the perspiration with the computation device;

detecting the first component from the perspiration with the detection device after the rate of change of concentration of the second component and a threshold value are compared and the rate of change of concentration of the second component becomes smaller than the threshold value;

calculating a concentration in the perspiration of the first component with the computation device;

converting the calculated concentration in the perspiration of the first component to a concentration of the first component in blood of a body; and executing a process of outputting the concentration in the blood of the first component with the computation device.

* * * * *